United States Patent
Li

(10) Patent No.: US 9,045,752 B2
(45) Date of Patent: Jun. 2, 2015

(54) NKX3-1 SARNA AND KLF4 SARNA AND USES THEREOF

(75) Inventor: Long-Cheng Li, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 113 days.

(21) Appl. No.: 13/583,905

(22) PCT Filed: Mar. 8, 2011

(86) PCT No.: PCT/US2011/027587
§ 371 (c)(1),
(2), (4) Date: Nov. 15, 2012

(87) PCT Pub. No.: WO2011/112607
PCT Pub. Date: Sep. 15, 2011

(65) Prior Publication Data
US 2013/0096184 A1 Apr. 18, 2013

Related U.S. Application Data

(60) Provisional application No. 61/313,019, filed on Mar. 11, 2010.

(51) Int. Cl.
| | | |
|---|---|---|
| A61K 31/70 | (2006.01) | |
| C07H 21/04 | (2006.01) | |
| C07H 21/02 | (2006.01) | |
| C12N 15/113 | (2010.01) | |
| A61K 31/7105 | (2006.01) | |
| C12N 15/67 | (2006.01) | |
| C12Q 1/68 | (2006.01) | |

(52) U.S. Cl.
CPC ........ *C12N 15/113* (2013.01); *C12N 2310/113* (2013.01); *A61K 31/7105* (2013.01); *C12N 15/67* (2013.01); *C12N 2310/11* (2013.01)

(58) Field of Classification Search
None
See application file for complete search history.

(56) References Cited

U.S. PATENT DOCUMENTS

| | | | |
|---|---|---|---|
| 5,614,396 A | 3/1997 | Bradley et al. | |
| 5,624,803 A | 4/1997 | Noonberg et al. | |
| 5,889,136 A | 3/1999 | Scaringe et al. | |
| 6,008,400 A | 12/1999 | Scaringe et al. | |
| 2004/0005593 A1 | 1/2004 | Lorens | |
| 2005/0048647 A1 | 3/2005 | Taira | |
| 2005/0060771 A1 | 3/2005 | Farmer | |
| 2007/0161031 A1 | 7/2007 | Trinklein et al. | |
| 2010/0210707 A1* | 8/2010 | Li et al. | 514/44 A |

FOREIGN PATENT DOCUMENTS

WO WO 2006/113246 10/2006

OTHER PUBLICATIONS

Abate-Shen et al., "Integrating differentiation and cancer: the Nkx3.1 homeobox gene in prostate organogenesis and carcinogenesis," Differentiation 76(6):717-727 (2008).
Abdulkadir et al., "Conditional Loss of Nkx3.1 in Adult Mice Induces Prostatic Intraepithelial Neoplasia," Mol Cell Biol 22(5):1495-1503 (2002).
Aigner, "Gene silencing through RNA interference (RNAi) in vivo: Strategies based on the direct application of siRNAs," J Biotechnol 124:12-25 (2006).
Akaogi et al., "KLF4 suppresses estrogen-dependent breast cancer growth by inhibiting the transcriptional activity of ERα," Oncogene 28:2894-2902 (2009).
Asatiani et al., "Deletion, Methylation, and Expression of the NKX3.1 Suppressor Gene in Primary Human Prostate Cancer," Cancer Res 65(4):1164-1173 (2005).
Bethel et al., "Decreased NKX3.1 Protein Expression in Focal Prostatic Atrophy, Prostatic Intraepithelial Neoplasia, and Adenocarcinoma: Association with Gleason Score and Chromosome 8p Deletion," Cancer Res 66(22):10683-10690 (2006).
Bhatia-Gaur et al., "Roles for Nkx3.1 in prostate development and cancer," Genes Dev 13:966-977 (1999).
Bieberich et al., "Prostate-specific and Androgen-dependent Expression of a Novel Homeobox Gene," J Biol Chem 271(50):31779-31782 (1996).
Bowen et al., "Loss of NKX3.1 Expression in Human Prostate Cancers Correlates with Tumor Progression," Cancer Res 60:6111-6115 (2000).
Breitbart et al., "Intricate combinatorial patterns of exon splicing generate multiple regulated troponin T isoforms from a single gene," Cell 41:67-82 (1985).
Brinster et al, "Introns increase transcriptional efficiency in transgenic mice," Proc Natl Acad Sci USA 85:836-840 (1988).
Brummelkamp et al., "A System for Stable Expression of Short Interfering RNAs in Mammalian Cells," Science 296(5567):550-553 (2002).
Bunz et al., "Requirement for p53 and p21 to Sustain G2 arrest after DNA Damage," Science 282(5393):1497-1501 (1998).
Check, "RNA interference: Hitting the on switch," Nature 448:855-858 (2007).
Chen et al., "Kruppel-like factor 4 (Gut-enriched Kruppel-like Factor) Inhibits Cell Proliferation by Blocking G1/S Progression of the Cell Cycle," J Biol Chem 276(32):30423-30428 (2001).
Chen et al., "Transcriptional Profiling of Kruppel-like Factor 4 Reveals a Function in Cell Cycle Regulation and Epithelial Differentiation," J Mol Biol 326(3):665-677 (2003).
Chen et al., "Antitumor effect of dsRNA-induced p21WAF1/CIP1 gene activation in human bladder cancer cells," Mol Cancer Ther 7(3):698-703 (2008).

(Continued)

*Primary Examiner* — Sean McGarry
(74) *Attorney, Agent, or Firm* — Edward J. Baba; Shweta Chandra; Bozicevic, Field & Francis LLP

(57) ABSTRACT

The present disclosure provides compositions, pharmaceutical preparations, kits and methods for increasing expression of a NKX3-1 gene product in a cell by contacting the cell with a small activating RNA (saRNA) molecule comprising a ribonucleic strand that is complementary to a promoter region sequence of the NKX3-1 gene. The present disclosure also provides compositions, pharmaceutical preparations, kits and methods for increasing expression of a KLF4 gene product in a cell by contacting the cell with a small activating RNA (saRNA) molecule comprising a ribonucleic strand that is complementary to a promoter region sequence of the KLF4 gene.

25 Claims, 16 Drawing Sheets

(56) References Cited

OTHER PUBLICATIONS

Clark et al., "Enhancing the Efficiency of Transgene Expression," Phil Trans R Soc Lond B 339:225-232 (1993).
Dang et al., "Overexpression of Kruppel-like factor 4 in the human colon cancer cell line RKO leads to reduced tumorigenecity," Oncogene 22:3424-3430 (2003).
Dhanasekaran et al., "Delineation of prognostic biomarkers in prostate cancer," Nature 412:822-826 (2001).
Dhanasekaran et al., "Molecular profiling of human prostate tissues: insights into gene expression patterns of prostate development during puberty," FASEB J 19(2):243-245 (2005).
Evans and Liu, "Roles of Kruppel-like factor 4 in normal homeostasis, cancer and stem cells," Acta Biochim Biophys Sin 40(7):554-564 (2008).
Evans et al., "Kruppel-like Factor 4 Is Acetylated by p300 and Regulates Gene Transcription via Modulation of Histone Acetylation," J Biol Chem 282(47):33994-34002 (2007).
Faria et al., "Phosphoramidate oligonucleotides as potent antisense molecules in cells and in vivo," Nature Biotechnol 19:40-44 (2001).
Foster et al., "Induction of KLF4 in basal keratinocytes blocks the proliferation-differentiation switch and initiates squamous epithelial dysplasia," Oncogene 24:1491-1500 (2005).
Ghaleb et al., "Kruppel-like factor 4 exhibits antiapoptotic activity following gamma-radiation-induced DNA damage," Oncogene 26:2365-2373 (2007).
Ghaleb et al., "Haploinsufficiency of Kruppel-Like Factor 4 Promotes Adenomatous Polyposis Coli-Dependent Intestinal Tumorigenesis," Cancer Res 67(15):7147-7154 (2007).
Hagos et al., "Mouse embryonic fibroblasts null for the Kruppel-like factor 4 gene are genetically unstable," Oncogene 28:1197-1205 (2009).
Harvey, "NK-2 homeobox genes and heart development," Dev Biol 178:203-216 (1996).
He et al., "A Novel Human Prostate-Specific, Androgen-Regulated Homeobox Gene (NKX3.1) That Maps to 8p21, a Region Frequently Deleted in Prostate" Genomics 43:69-77(1997).
Hu et al., "Putative Tumor-Suppressive Function of Kruppel-Like Factor 4 in Primary Lung Carcinoma," Clin Cancer Res 15(18):5688-5695 (2009).
Huang et al., "KLF4 and PCNA identify stages of tumor initiation in a conditional model of cutaneous squamous epithelial neoplasia," Cancer Biol Ther 4(12):1401-1408 (2005).
Huang et al, "RNAa Is Conserved in Mammalian Cells," PLoS One 5(1):e8848 pp. 1-8 (2010).
Ishkanian et al., "High-resolution array CGH identifies novel regions of genomic alteration in intermediate-risk prostate cancer," The Prostate 69:1091-1100 (2009).
Janowski et al., "Inhibiting gene expression at transcription start sites in chromosomal DNA with antigene RNAs," Nat Chem Biol 1(4):216-222 (2005).
Janowski et al., "Activating gene expression in mammalian cells with promoter-targeted duplex RNAs," Nat Chem Biol 3(3):166-173 (2007).
Karpanen et al., "Vascular Endothelial Growth Factor C Promotes Tumor Lymphangiogenesis and Intralymphatic Tumor Growth," Cancer Res 61:1786-1790 (2001).
Katz et al., "Loss of Klf4 in mice causes altered proliferation and differentiation and precancerous changes in the adult stomach," Gastroenterology 128(4):935-945 (2005).
Kharas et al., "KLF4 suppresses transformation of pre-B cells by ABL oncogenes," Blood 109(2):747-755 (2007).
Kim et al., "MicroRNA-directed transcriptional gene silencing in mammalian cells," PNAS 105(42):16230-16235 (2008).
Kim et al., "Argonaute-1 directs siRNA-mediated transcriptional gene silencing in human cells," Nature Structural & Molecular Biology 13(9):793-797 (2006).
Kim et al., "Nkx3.1 Mutant Mice Recapitulate Early Stages of Prostate Carcinogenesis," Cancer Res 62:2999-3004 (2002).

Kinkade et al, "Targeting AKT/mTOR and ERK MAPK signaling inhibits hormone-refractory prostate cancer in a preclinical mouse model," J Clin Invest 118(9):3051-3064 (2008).
Korkmaz et al., "Full-length cDNA sequence and genomic organization of human NKX3A—alternative forms and regulation by both androgens and estrogens," Gene 260:25-36 (2000).
Kuslak and Marker, "Fibroblast growth factor receptor signaling through MEK-ERK is required for prostate bud induction," Differentiation 75:638-651 (2007).
Lee et al, "Expression of small interfering RNAs targeted against HIV-1 rev transcripts in human cells," Nat Biotechnol 20:500-505 (2002).
Leff and Rosenfeld, "Complex Transcriptional Units: Diversity in Gene Expression by Alternative RNA Processing," Ann Rev Biochem 55:1091-1117 (1986).
Lei et al, "NKX3.1 stabilizes p53, inhibits AKT activation, and blocks prostate cancer initiation caused by PTEN loss," Cancer Cell 9(5):367-378 (2006).
Li, "The multifaceted small RNAs," RNA Biol 5(2):61-64 (2008).
Li and Dahiya, "MethPrimer: designing primers for methylation PCRs," Bioinformatics 18(11):1427-1431 (2002).
Li et al "Small dsRNAs induce transcriptional activation in human cells," PNAS 103(46):17337-17342 (2006).
Lind et al., "The loss of NKX3.1 expression in testicular—and prostate—cancers is not caused by promoter hypermethylation," Mol Cancer 4:8, 5 pgs (2005).
Liu et al., KLF4 regulates the expression of interleukin-10 in RAW264.7 macrophages, Biochem Biophys Res Comm 362:575-581 (2007).
Lundgren et al., "Cytogenetic Analysis of 57 Primary Prostatic Adenocarcinomas," Genes Chromosomes & Cancer 4:16-24 (1992).
MacGrogan et al., "Loss of Cromosome Arm 8p Loci in Prostate Cancer: Mapping by Quantitative Allelic Imbalance," Genes Chromosomes & Cancer 10:151-159 (1994).
Mao et al., "Up-regulation of E-cadherin by small activating RNA inhibits cell invasion and migration in 5637 human bladder cancer cells," Biochem Biophys Res Commun 375:466-470 (2008).
Matsuoka et al., "p57KIP2, a structurally distinct member of the p21CIP1 Cdk inhibitor family, is a candidate tumor suppressor gene," Genes Dev 9(6):650-662 (1995).
Misra and Pizzo, "Epac1-induced cellular proliferation in prostate cancer cells is mediated by B-Raf/ERK and mTOR signaling cascades," J Cell Biochem 108:998-1011 (2009).
Miyagishi and Taira, "U6 promoter—driven siRNAs with four uridine 3' overhangs efficiently suppress targeted gene expression in mammalian cells," Nat Biotechnol 20:497-500 (2002).
Morris et al., "Small Interfering RNA-Induced Transcriptional Gene Silencing in Human Cells," Science 305(5688):1289-1292 (2004).
Nakahara et al., "Genetic and Epigenetic Inactivation of Kruppel-like Factor 4 in Medulloblastoma," Neoplasia 12(1):20-27 (2010).
Napoli et al., "Promoter-specific transcriptional interference and c-myc gene silencing by siRNAs in human cells," EMBO J 28:1708-1719 (2009).
Oh et al., "Cholesterol level of lipid raft microdomains regulates apoptotic cell death in prostate cancer cells through EGFR-mediated Akt and ERK signal transduction," The Prostate 67:1061-1069 (2007).
Paddison et al., "Short hairpin RNAs (shRNAs) induce sequence-specific silencing in mammalian cells," Genes Dev 16:948-958 (2002).
Paul et al., "Effective expression of small interfering RNA in human cells," Nat Biotechnol 20:505-508 (2002).
Place et al., "MicroRNA-373 induces expression of genes with complementary promoter sequences," PNAS 105(5):1608-1613 (2008).
Ramaswamy et al., "A molecular signature of metastasis in primary solid tumors," Nat Genet 33:49-54 (2003).
Ramaswamy et al., "Multiclass cancer diagnosis using tumor gene expression signatures," PNAS 98(26):15149-15154 (2001).
Rhodes et al., "Oncomine 3.0: Genes, Pathways, and Networks in a Collection of 18,000 Cancer Gene Expression Profiles," Neoplasia 9(2):166-180 (2007).

(56) References Cited

OTHER PUBLICATIONS

Rowland et al., "The KLF4 tumour suppressor is a transcriptional repressor of p53 that acts as a context-dependent oncogene," Nat Cell Biol 7(11):1074-1082 (2005).
Rowland and Peeper, "KLF4, p21 and context-dependent opposing forces in cancer," Nat Rev Cancer 6(1):11-23 (2006).
Schneider et al., "Targeted disruption of the Nkx3.1 gene in mice results in morphogenetic defects of minor salivary glands: parallels to glandular duct morphogenesis in prostate," Mech Dev 95(1-2):163-174 (2000).
Shields et al., "Identification and Characterization of a Gene Encoding a Gut-enriched Kruppel-like Factor Expressed during Growth Arrest," J Biol Chem 271(33):20009-20017 (1996).
Skobe et al., "Induction of tumor lymphangiogenesis by VEGF-C promotes breast cancer metastasis," Nat Med 7(2):192-198 (2001).
Steadman et al., "DNA-binding sequence of the human prostate-specific homeodomain protein NKX3.1," Nucleic Acids Res 28(12):2389-2395 (2000).
Stemmler et al., "E-cadherin intron 2 contains cis-regulatory elements essential for gene expression," Development 132(5):965-976 (2005).
Takahashi et al "Induction of Pluripotent Stem Cells from Adult Human Fibroblasts by Defined Factors," Cell 131(5):861-872 (2007).
Tanaka et al., "Nkx3.1, a murine homolog of Ddrosophila bagpipe, regulates epithelial ductal branching and proliferation of the prostate and palatine glands," Dev Dyn 219:248-260 (2000).
Thierry-Mieg and Thierry-Mieg, "AceView: a comprehensive cDNA-supported gene and transcripts annotation." Genome Biol 7(Suppl 1):512.1-512.14 (2006).
Thomson and Cunha, "Prostatic growth and development are regulated by FGFIO," Development 126:3693-3701 (1999).
Thomson, "Role of androgens and fibroblast growth factors in prostatic development," Reproduction 121:187-195 (2001).
Tian et al., "MICRORNA-10B promotes human esophageal cancer cell migration and invasion through KLF4," J Biol Chem, 18pgs (2010).
Tomlins et al., "Integrative molecular concept modeling of prostate cancer progression," Nat Genet 39(1):41-51 (2007).
Toulme, "New candidates for true antisense," Nat Biotechnol 19:17-18 (2001).
True et al., "A molecular correlate to the Gleason grading system for prostate adenocarcinoma," PNAS 103(29):10991-10996 (2006).
Turunen et al., "Efficient Regulation of VEGF Expression by Promoter-Targeted Lentiviral shRNAs Based on Epigenetic Mechanism: A Novel Example of Epigenetherapy," Circ Res 105(6):604-609 (2009).
Tuschl, "Expanding small RNA interference," Nat Biotechnol 20:446-448 (2002).
Vanaja et al., "Transcriptional Silencing of Zinc Finger Protein 185 Identified by Expression Profiling is Associated with Prostate Cancer Progression," Cancer Res 63:3877-3882 (2003).
Varambally et al., "Integrative genomic and proteomic analysis of prostate cancer reveals signatures of metastatic progression," Cancer Cell 8(5):393-406 (2005).
Voeller et al., "Coding Region of NKX3.1, a Prostate-Specific Homeobox Gene on 8p21, Is Not Mutated in Human Prostate Cancers," Cancer Res 57(20):4455-4459 (1997).
Wang et al., "Prognostic Value and Function of KLF4 in Prostate Cancer: RNAa and Vector-Mediated Overexpression Identify KLF4 as an Inhibitor of Tumor Cell Growth and Migration," Cancer Res 70(24):10182-10191 (2010).
Wassmann et al., "Induction of p53 by GKLF is essential for inhibition of proliferation of vascular smooth muscle cells," J Mol Cell Cardiol 43:301-307 (2007).
Wegiel et al., "Cystatin C is Downregulated in Prostate Cancer and Modulates Invasion of Postate Cancer Cells via MAPK/Erk and Androgen Receptor Pathways," PLoS One 4(11):e7953 10pgs (2009).
Wei et al., "Drastic Down-regulation of Kruppel-Like Factor 4 Expression is Critical in Human Gastric Cancer Development and Progression," Cancer Res 65(7):2746-2754 (2005).
Wei et al., "Emerging role of KLF4 in human gastrointestinal cancer," Carcinogenesis 27(1):23-31 (2006).
Wei et al., "Kruppel-like Factor 4 Induces p27Kip1 Expression in and Suppresses the Growth and Metastasis of Human Pancreatic Cancer Cells," Cancer Res 68(12):4631-4639 (2008).
Yang et al., "Up-regulation of p21WAF1/Cip1 by saRNA induces G1-phase arrest and apoptosis in T24 human bladder cancer cells," Cancer Letters 265:206-214 (2010).
Yang et al., "KLF4 and KLF5 Regulate Proliferation, Apoptosis and Invasion in Esophageal Cancer Cells," Cancer Biol Ther 4(11): 1216-1221 (2005).
Yoon et al., "Kruppel-like Factor 4 Mediates p53-dependent G1/S Cell Cycle Arrest in Response to DNA Damage," J Biol Chem 278(4):2101-2105 (2003).
Yoon and Yang, "Requirement of Kruppel-like Factor 4 in Preventing Entry into Mitosis following DNA Damage," J Biol Chem 279(6):5035-5041 (2004).
Yu et al., "Gene Expression Alterations in Prostate Cancer Predicting Tumor Aggression and Preceding Development of Malignancy," J Clin Onco 22(14):2790-2799 (2004).
Zhang et al., "Loss of NKX3.1 Favors Vascular Endothelial Growth Factor-C Expression in Prostate Cancer," Cancer Res 68(21):8770-8778 (2008).
Zhang et al., "Gene expression profiles in the PC-3 human prostate cancer cells induced by NKX3.1," Mol Biol Rep 37:1505-1512 (2010).
Zhang et al., "The Gut-enriched Kruppel-like Factor (Kruppel-like Factor 4) Mediates the Transactivating Effect of p53 on the p21 WAF1/Cip1 Promoter," J Biol Chem 275(24):18391-18398 (2000).
Zhao et al., "Identification of Kruppel-like factor 4 as a potential tumor suppressor gene in colorectal cancer," Oncogene 23:395-402 (2004).

\* cited by examiner

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 1
gacgguccug aagagcuaat t                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 2
uuagcucuuc aggaccguct t                                              21

<210> SEQ ID NO 3
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 3
gacuguuugu cuugaucgut t                                              21

<210> SEQ ID NO 4
<211> LENGTH: 21
```

-continued

```
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 4
acgaucaaga caaacaguct t                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 5
gaacccaggg agccgacaat t                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 6
uugucggcuc ccuggguuct t                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 7
cgcugacccc accagucuut t                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 8
aagacuggug gggucagcgt t                                              21

<210> SEQ ID NO 9
```

```
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 9
gcuguagcga aggaaguuat t                                      21

<210> SEQ ID NO 10
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 10
uaacuuccuu cgcuacagct t                                      21

<210> SEQ ID NO 11
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 11
gauuuagcug ccauagcaat t                                      21

<210> SEQ ID NO 12
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 12
uugcuauggc agcuaaauct t                                      21

<210> SEQ ID NO 13
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 13
acuacugagu gacaguagat t                                      21
```

```
<210> SEQ ID NO 14
<211> LENGTH: 21
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_RNA
<222> LOCATION: (1)..(19)
<223> OTHER INFORMATION: Nucleotides 1-19 are RNA

<400> SEQUENCE: 14
ucuacuguca cucaguagut t                                              21

<210> SEQ ID NO 15
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 15
acccacactt gtgattacgc                                                20

<210> SEQ ID NO 16
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 16
ccgtgtgttt acggtagtgc                                                20

<210> SEQ ID NO 17
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 17
tgcaaggaac ggaatttaca                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 18
acctggctga gaatccacac                                                20

<210> SEQ ID NO 19
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 19
ttatctgctg gcttggcact                                                20

<210> SEQ ID NO 20
<211> LENGTH: 20
<212> TYPE: DNA
```

```
<213> ORGANISM: Artificial sequence
<220> FEATURE:
<223> OTHER INFORMATION: Synthetic Nucleic Acid

<400> SEQUENCE: 20
gcagcaaccc caaagtaatc                                               20

<210> SEQ ID NO 21
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 21
gatgacagtg cacccagaga                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 22
ccgactcttc ccatttttca                                               20

<210> SEQ ID NO 23
<211> LENGTH: 23
<212> TYPE: DNA
<213> ORGANISM: Artificial sequence
<220> FEATURE:
<223> OTHER INFORMATION: Synthetic Nucleic Acid

<400> SEQUENCE: 23
cagaaccgct gggattacga ctt                                           23

<210> SEQ ID NO 24
<211> LENGTH: 24
<212> TYPE: DNA
<213> ORGANISM: Artificial sequence
<220> FEATURE:
<223> OTHER INFORMATION: Synthetic Nucleic Acid

<400> SEQUENCE: 24
agtcgctgtc cacttcggtc cact                                          24

<210> SEQ ID NO 25
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 25
tgggtgtgaa ccatgagaag                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 26
gtgtcgctgt tgaagtcaga                                               20
```

```
<210> SEQ ID NO 27
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 27
gcaaagacct gtacgccaac                                           20

<210> SEQ ID NO 28
<211> LENGTH: 20
<212> TYPE: DNA
<213> ORGANISM: Artificial sequence
<220> FEATURE:
<223> OTHER INFORMATION: Synthetic Nucleic Acid

<400> SEQUENCE: 28
gtacttgcgc tcaggaggag                                           20

<210> SEQ ID NO 29
<211> LENGTH: 23
<212> TYPE: DNA
<213> ORGANISM: Artificial sequence
<220> FEATURE:
<223> OTHER INFORMATION: Synthetic Nucleic Acid

<400> SEQUENCE: 29
ggagatggag ggttggatga gtt                                       23

<210> SEQ ID NO 30
<211> LENGTH: 23
<212> TYPE: DNA
<213> ORGANISM: Artificial sequence
<220> FEATURE:
<223> OTHER INFORMATION: Synthetic Nucleic Acid
<220> FEATURE:
<221> NAME/KEY: misc_feature
<222> LOCATION: (1)..(23)
<223> OTHER INFORMATION: degenerate nucleic acid where r at positions 5
      and 23 can be "g" or "a"

<400> SEQUENCE: 30
taacrccaac caaacaacta acr                                       23
```

NKX3-1 SARNA AND KLF4 SARNA AND USES THEREOF

GOVERNMENT RIGHTS

This invention was made with government support under Grants No. R01 CA111470-01 and R21 CA131774-02 awarded by the National Institutes of Health. The government has certain rights in the invention.

BACKGROUND OF THE INVENTION

Relatively recent discoveries in the field of RNA metabolism have revealed that the uptake of certain double stranded RNA (dsRNA) can induce a phenomenon known as RNA interference (RNAi). RNAi is a process by which a polynucleotide directly or indirectly inhibits the expression of a gene, e.g., through inhibiting translation of messenger RNA. This phenomenon has been observed in cells of a diverse group of organisms, including *C. elegans, Drosophila,* and humans, providing a powerful therapeutic approach to the genetic control of human disease.

It has been shown that when short RNA duplexes are introduced into mammalian cells in culture, sequence-specific inhibition of target mRNA can be accomplished without inducing an interferon response.

These short dsRNAs, referred to as small interfering RNAs (siRNAs), can, for example, act catalytically at sub-molar concentrations to cleave greater than 95% of the target mRNA in a cell. RNA-induced gene silencing in mammalian cells is presently believed to implicate at least one of three different levels of control: (i) transcription inactivation (siRNA-guided DNA and histone modification, for example, methylation); (ii) siRNA-induced mRNA degradation; and (iii) mRNA-induced transcriptional attenuation. Consequently, the ability to assess gene function via siRNA mediated methods, as well as to develop therapies based on siRNA-induced gene silencing, presents an exciting and valuable tool that will accelerate genome-wide investigations across a broad range of biomedical and biological research. However, application of the technology has been limited to gene silencing and has not been applied to gene activation.

There is accordingly still a need for compounds that can activate gene expression, and methods of using such compounds for the study and treatment of genetic disorders. The present invention addresses these needs, as well as others.

SUMMARY OF THE INVENTION

The present disclosure provides compositions, pharmaceutical preparations, kits and methods for increasing expression of NKX3-1 gene product in a cell by contacting the cell with a small activating RNA (saRNA) molecule comprising a ribonucleic strand that is complementary to a promoter region sequence of the NKX3-1 gene. The present disclosure provides also compositions, pharmaceutical preparations, kits and methods for increasing expression of KLF4 gene product in a cell by contacting the cell with a small activating RNA (saRNA) molecule comprising a ribonucleic strand that is complementary to a promoter region sequence of the KLF4 gene.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
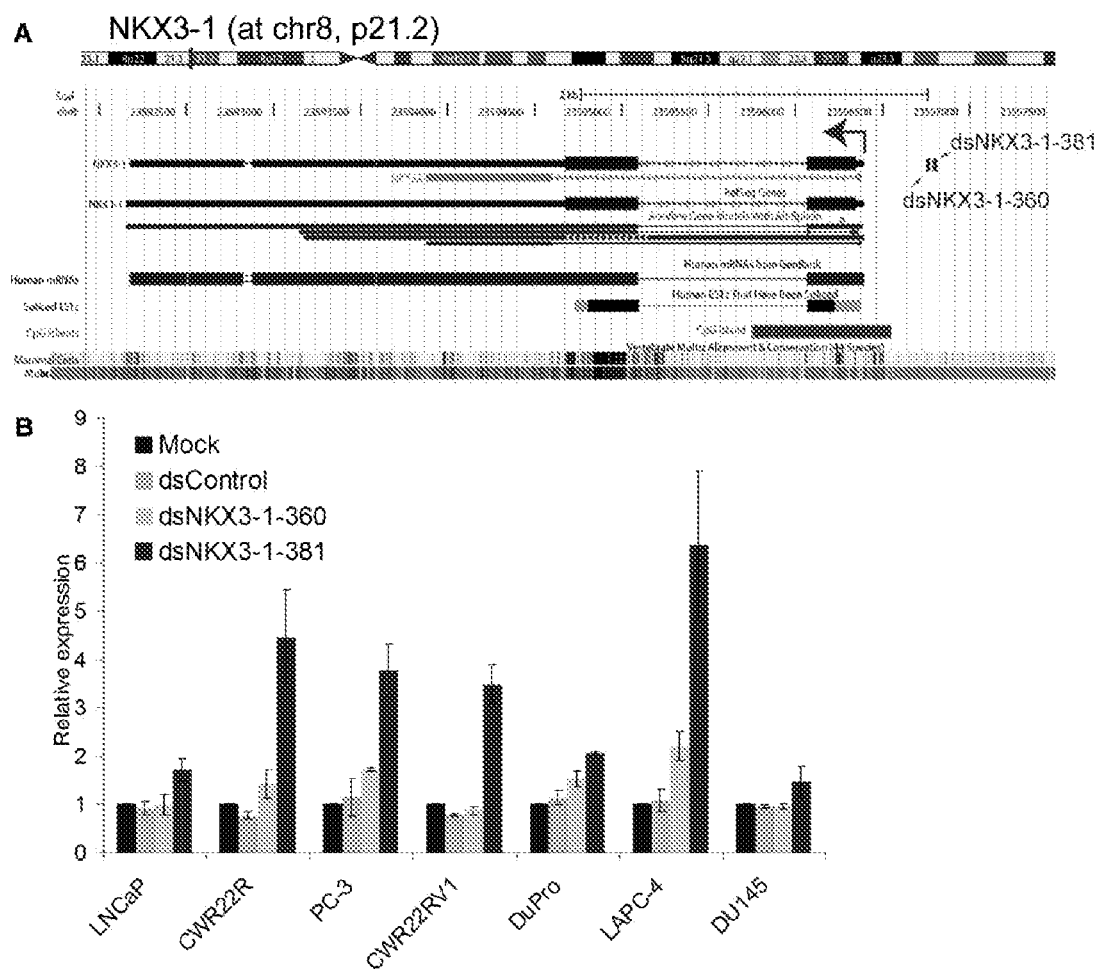
FIG. 1, panel A is a schematic representation of NKX3-1 gene. The location of two saRNAs targeting the promoter at positions −381 and −360 is indicated. Panel B shows relative NKX3-1 mRNA expression (compared to mock), assayed by quantitative RT-PCR (qPCR), in cells transfected with mock (first bar from the left), dsRNA control (second bar from the left), dsNKX3-1-360 (third bar from the left), and dsNKX3-1-381 (fourth bar from the left). The results are means±SEM of at least two independent experiments and plotted as relative expression compared to mock transfection in each cell line.

The present disclosure provides compositions, pharmaceutical preparations, and methods for increasing expression of a NKX3-1 gene product through transcriptional activation of the encoding gene in a cell by contacting the cell with a small activating RNA (saRNA) molecule comprising a ribonucleic strand that is complementary to a promoter region sequence of the NKX3-1 gene. The present disclosure also provides compositions, pharmaceutical preparations, and methods for increasing expression of a KLF4 gene product through transcriptional activation of the encoding gene in a cell by contacting the cell with a small activating RNA (saRNA) molecule comprising a ribonucleic strand that is complementary to a sequence of the promoter region of the KLF4 gene. Also provided are kits for practicing the subject methods of the invention.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a molecule" includes a plurality of such molecules and reference to "the molecule" includes reference to one or more molecules and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein the term "isolated" is meant to describe a compound of interest (e.g., either a polynucleotide or a polypeptide) that is in an environment different from that in which the compound might naturally occur.

"Purified" as used herein refers to a compound removed from an environment in which it was produced and is at least 60% free, preferably 75% free, and most preferably 90% free from other components with which it is naturally associated or with which it was otherwise associated with during production.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes.

Perfect complementarity or 100% complementarity refers to the situation in which each nucleotide unit of one polynucleotide strand can hydrogen bond with a nucleotide unit of a second polynucleotide strand, without a "mismatch". Less than perfect complementarity refers to the situation in which not all nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. Substantial complementarity refers to about 79%, about 80%, about 85%, about 90%, about 95%, or greater complementarity. Thus, for example, two polynucleotides of 29 nucleotide units each, wherein each comprises a di-dT at the 3' terminus such that the duplex region spans 27 bases, and wherein 27 of the 27 bases of the duplex region on each strand are complementary, are substantially complementary. In determining complementarity, overhang regions are excluded.

The term "conjugate" refers to a polynucleotide that is covalently or non-covalently associated with a molecule or moiety that alters the physical properties of the polynucleotide, such as increasing stability and/or facilitate cellular uptake of a double stranded RNA, for example, but does not significantly affect the ability of the polynucleotide to base pair with a complementary polynucleotide. A "terminal conjugate" may have a molecule or moiety attached directly or indirectly through a linker to a 3' and/or 5' end of a polynucleotide or double stranded polynucleotide. An internal conjugate may have a molecule or moiety attached directly or indirectly through a linker to a base, to the 2' position of the ribose, for example, or to other positions that do not interfere with Watson-Crick base pairing, for example, 5-aminoallyl uridine.

In a double stranded polynucleotide, one or both 5' ends of the strands of polynucleotides comprising the double stranded polynucleotide can bear a conjugated molecule or moiety, and/or one or both 3' ends of the strands of polynucleotides comprising the double stranded polynucleotide can bear a conjugated molecule or moiety.

Conjugates may contain, for example, amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates are steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecandiol or undecyl groups, phospholipids such as di-hexadecyl-rac-glycerol, triethylammonium 1,2-di-O-hexadecyl-rac-glycer-o-3-H-phosphonate, polyamines, polyethylene glycol, adamantane acetic acid, palmityl moieties, octadecylamine moieties, hexylaminocarbonyl-oxyc-holesterol, farnesyl, geranyl and geranylgeranyl moieties.

Conjugates can also comprise a detectable label. For example, conjugates can be a polynucleotide covalently attached to a fluorophore. Conjugates may include fluorophores such as TAMRA, BODIPY, Cyanine derivatives such as Cy3 or Cy5, Dabsyl, or any other suitable fluorophore known in the art.

A conjugate molecule or moiety may be attached to any position on the terminal nucleotide that is convenient and that does not substantially interfere with the desired activity of the polynucleotide(s) that bear it, for example the 3' or 5' position of a ribosyl sugar. A conjugate molecule or moiety substantially interferes with the desired activity of a saRNA if it adversely affects its functionality such that the ability of the saRNA to mediate gene activation is reduced, for example, by greater than 80% in an in vitro assay employing cultured cells, where the functionality is measured at 24 hours post transfection.

The phrase "effective concentration" refers to a concentration of saRNA in a cell effective to cause an increase in transcription of a gene of interest in the cell. Of particular interest is an effective concentration that provides a greater than or equal to at least about 10% or more, 20% or more, 30% or more, 45% or more increase, including about 50% or more, about 60% or more, about 70% or more, about 75% or more, about 80% or more increase in target sequence activity relative to a basal expression level at 24, 48, 72, or 96 hours following administration. Target sequence activity may be measured by any method known in the art. For example, where the target sequence is a promoter, target sequence activity may be measured by level of transcription, level of the protein whose transcription is operably linked or operably associated with the promoter, or activity of the protein whose transcription is operably linked or operably associated with the promoter.

The term "polynucleotide" refers to polymers of nucleotides, and includes but is not limited to single stranded or double stranded molecule of DNA, RNA, or DNA/RNA hybrids including polynucleotide chains of regularly and irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides wherein the substitution or attachment of various entities or moieties to the nucleotide units at any position, as well as naturally-occurring or non-naturally occurring backbones, are included.

The term "polyribonucleotide" refers to a polynucleotide comprising two or more modified or unmodified ribonucleotides and/or their analogs.

The phrases "operably associated" and "operably linked" refer to functionally related nucleic acid sequences. By way of example, a regulatory sequence is operably linked or operably associated with a protein encoding nucleic acid sequence if the regulatory sequence can exert an effect on the expression of the encoded protein. In another example, a promoter is operably linked or operably associated with a protein encoding nucleic acid sequence if the promoter controls the transcription of the encoded protein. While operably associated or operably linked nucleic acid sequences can be contiguous with the nucleic acid sequence that they control, the phrases "operably associated" and "operably linked" are not meant to be limited to those situations in which the regulatory sequences are contiguous with the nucleic acid sequences they control.

The term "gene" as used herein includes sequences of nucleic acids that when present in an appropriate host cell facilitates production of a gene product. "Genes" can include nucleic acid sequences that encode proteins, and sequences that do not encode proteins, and includes genes that are endogenous to a host cell or are completely or partially recombinant (e.g., due to introduction of an exogenous polynucleotide encoding a promoter and a coding sequence, or introduction of a heterologous promoter adjacent an endogenous coding sequence, into a host cell). For example, the term "gene" includes nucleic acid that can be composed of exons and introns. Sequences that code for proteins are, for example, sequences that are contained within exons in an open reading frame between a start codon and a stop codon., "Gene" as used herein refers to a nucleic acid that includes, for example, regulatory sequences such as promoters, enhancers and all other sequences known in the art that control the transcription, expression, or activity of a nucleic acid sequence operably linked or operably associated to the regulatory sequence, whether the nucleic acid sequence comprises coding sequences or non-coding sequences. In one context, for example, "gene" may be used to describe a nucleic acid comprising regulatory sequences such as promoter or enhancer and coding and non-coding sequences. The expression of a recombinant gene may be controlled by one or more heterologous regulatory sequences. "Heterologous" refers to two elements that are not normally associated in nature.

A "target gene" is a nucleic acid containing a sequence, such as, for example, a promoter or enhancer, against which a saRNA can be directed for the purpose of affecting activation of expression. Either or both "gene" and "target gene" may be nucleic acid sequences naturally occurring in an organism, transgenes, viral or bacterial sequences, chromosomal or extrachromosomal, and/or transiently or chronically transfected or incorporated into the cell and/or its chromatin. A "target gene" can, upon saRNA-mediated activation, repress the activity of another "gene" such as a gene coding for a protein (as measured by transcription, translation, expression, or presence or activity of the gene's protein product). In another example, a "target gene" can comprise an enhancer, and saRNA mediated activation of the enhancer may increase the functionality of an operably linked or operably associated promoter, and thus increase the activity of another "gene" such as a gene coding for a protein that is operably linked to the increased promoter and/or enhancer.

"Regulatory elements" are nucleic acid sequences that regulate, induce, repress, or otherwise mediate the transcription, translation of a protein or RNA coded by a nucleic acid sequence with which they are operably linked or operably associated. Typically, a regulatory element or sequence such as, for example, an enhancer or repressor sequence, is operatively linked or operatively associated with a protein or RNA coding nucleic acid sequence if the regulatory element or regulatory sequence mediates the level of transcription, translation or expression of the protein coding nucleic acid sequence in response to the presence or absence of one or more regulatory factors that control transcription, translation and/or expression. Regulatory factors include, for example, transcription factors. Regulatory sequences may be found in introns.

Regulatory sequences or elements include, for example, "TATAA" boxes, "CAAT" boxes, differentiation-specific elements, cAMP binding protein response elements, sterol regulatory elements, serum response elements, glucocorticoid response elements, transcription factor binding elements such as, for example, SPI binding elements, and the like. A "CAAT" box is typically located upstream (in the 5' direction) from the start codon of a eukaryotic nucleic acid sequence encoding a protein or RNA. Examples of other regulatory sequences include splicing signals, polyadenylation signals, termination signals, and the like. Further examples of nucleic acid sequences that comprise regulatory sequences include the long terminal repeats of the Rous sarcoma virus and other retroviruses. An example of a regulatory sequence that controls tissue-specific transcription is the interferon-epsilon regulatory sequence that preferentially induces production of the operably linked sequence encoding the protein in placental, tracheal, and uterine tissues, as opposed to lung, brain, liver, kidney, spleen, thymus, prostate, testis, ovary, small intestine, and pancreatic tissues. Numerous regulatory sequences are known in the art, and the foregoing is merely illustrative of a few.

The term "enhancer" and phrase "enhancer sequence" refer to a variety of regulatory sequence that can increase the efficiency of transcription, without regard to the orientation of the enhancer sequence or its distance or position in space from the promoter, transcription start site, or first codon of the nucleic acid sequence encoding a protein with which the enhancer is operably linked or associated.

The term "promoter" refers to a nucleic acid sequence that does not code for a protein, and that is operably linked or operably associated to a protein coding or RNA coding nucleic acid sequence such that the transcription of the operably linked or operably associated protein coding or RNA coding nucleic acid sequence is controlled by the promoter. Typically, eukaryotic promoters comprise between 100 and 5,000 base pairs, although this length range is not meant to be limiting with respect to the term "promoter" as used herein. Although typically found 5' to the protein coding nucleic acid sequence to which they are operably linked or operably associated, promoters can be found in intron sequences as well. The term "promoter" is meant to include regulatory sequences operably linked or operably associated with the same protein or RNA encoding sequence that is operably linked or operably associated with the promoter. Promoters can comprise many elements, including regulatory elements. The term "promoter" comprises promoters that are inducible, wherein the transcription of the operably linked nucleic acid sequence encoding the protein is increased in response to an inducing agent. The term "promoter" may also comprise promoters that are constitutive, or not regulated by an inducing agent.

The phrase "non-coding target sequence" or "non-coding nucleic acid sequence" refers to a regulatory nucleic acid sequence of interest that is not contained within an exon of a gene. Examples of "non-coding target sequence" or "non-coding nucleic acid sequence" include promoter regions, enhancer regions, and the like.

"Nucleotide analogs" include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

"Modified bases" refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

The phrase "nucleotide unit" refers to a single nucleotide residue and is comprised of a modified or unmodified nitrogenous base, a modified or unmodified sugar, and a modified or unmodified moiety that allows for linking of two nucleotides together or a nucleotide to a conjugate that precludes further linkage. The single nucleotide residue may be in a polynucleotide. Thus, a polynucleotide having 27 bases has 27 nucleotide units.

The phrase "nuclear uptake enhancing modification" refers to a modification of a naturally occurring or non-naturally occurring polynucleotide that provides for enhanced nuclear uptake of the modified polynucleotide. An example of a "nuclear uptake enhancing modification" is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus. An effective concentration is a concentration that results in a detectable change in the transcription or activity of a gene or target sequence as the result of the accumulation of nucleic acid within the nucleus.

The phrases "orthoester protected" and "orthoester modified" refer to modification of a sugar moiety within a nucleotide unit with an orthoester. Preferably, the sugar moiety is a ribosyl moiety. In general, orthoesters have the structure $RC(OR')_3$ wherein each R' can be the same or different, R can be an H, and wherein the underscored C is the central carbon of the orthoester. The orthoesters of the present invention are comprised of orthoesters wherein a carbon of a sugar moiety in a nucleotide unit is bonded to an oxygen, which is in turn bonded to the central carbon of the orthoester. To the central carbon of the orthoester is, in turn, bonded two oxygens, such that in total three oxygens bond to the central carbon of the orthoester. These two oxygens bonded to the central carbon (neither of which is bonded to the carbon of the sugar moiety) in turn, bond to carbon atoms that comprise two moieties that can be the same or different. For example, one of the oxygens can be bound to an ethyl moiety, and the other to an isopropyl moiety. In one example, R can be an H, one R' can be a ribosyl moiety, and the other two R' moieties can be 2-ethyl-hydroxyl moieties. Orthoesters can be placed at any position on the sugar moiety, such as, for example, on the 2', 3' and/or 5' positions. Exemplary orthoesters, and methods of making orthoester protected polynucleotides, are described in U.S. Pat. Nos. 5,889,136 and 6,008,400, each herein incorporated by reference in its entirety.

The term "stabilized" refers to the ability of a dsRNA or saRNA to resist degradation while maintaining functionality and can be measured in terms of its half-life in the presence of, for example, biological materials such as serum. The half-life of an saRNA or an siRNA in, for example, serum refers to the time taken for the 50% of saRNA or siRNA to be degraded.

The phrase "duplex region" refers to the region in two complementary or substantially complementary polynucleotides that form base pairs with one another, either by Watson-Crick base pairing or any other manner that allows for a duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity generally refers to about at least 79%, about 80%, about 85%, about 85%, about 90%, about 95% or greater complementarity. For example, a mismatch in a duplex region consisting of 19 base pairs (i.e., 18 base pairs and one mismatch) results in about 94.7% complementarity, rendering the duplex region substantially complementary. In another example, three mismatches in a duplex region consisting of 19 base pairs (i.e., 16 base pairs and three mismatches) results in about 84.2% complementarity, rendering the duplex region substantially complementary, and so on.

The term "overhang" refers to a terminal (5' or 3') non-base pairing nucleotide resulting from one strand extending beyond the other strand within a doubled stranded polynucleotide. One or both of two polynucleotides that are capable of forming a duplex through hydrogen bonding of base pairs may have a 5' and/or 3' end that extends beyond the 3' and/or 5' end of complementarity shared by the two polynucleotides. The single-stranded region extending beyond the 3' and/or 5' end of the duplex is referred to as an overhang.

The phrase "gene silencing" refers to the reduction in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. "Gene silencing" refers to the reduction or amelioration of activity associated with a nucleic acid sequence, such as its ability to function as a regulatory sequence, its ability to be transcribed, its ability to be translated and result in expression of a protein, regardless of the mechanism whereby such silencing occurs.

As used herein, the terms "gene activating", "activating a gene", or "gene activation" are interchangeable and refer to an increase in transcription, translation or expression or activity of a nucleic acid, as measured by transcription level, mRNA level, enzymatic activity, methylation state, chromatin state or configuration, translational level, or other measure of its activity or state in a cell or biological system. Such activities or states can be assayed directly or indirectly. Furthermore, "gene activating", "activating a gene", or "gene activation" refer to the increase of activity associated with a nucleic acid sequence, such as its ability to function as a regulatory sequence, its ability to be transcribed and result in expression of a protein, regardless of the mechanism whereby such activation occurs.

The phrase "RNA interference" and the term "RNAi" refer to the process by which a polynucleotide or double stranded polynucleotide comprising at least one ribonucleotide unit exerts an effect on a biological process through disruption of gene expression. The process includes but is not limited to gene silencing by degrading mRNA, interactions with tRNA, rRNA, hnRNA, cDNA and genomic DNA, as well as methylation of DNA and ancillary proteins.

The term "siRNA" and the phrase "short interfering RNA" refer to a double stranded nucleic acid that is capable of performing RNAi and that is between 18 and 30 base pairs in length (i.e., a duplex region of between 18 and 30 base pairs). Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides. In contrast, the saRNAs of the invention are distinct from, and thus are not, siRNAs. saRNAs do not facilitate RNAi or gene silencing.

The phrase "mammalian cell" refers to a cell of any mammal, including humans. The phrase refers to cells in vivo, such as, for example, in an organism or in an organ of an organism. The phrase also refers to cells in vitro, such as, for example, cells maintained in cell culture.

The term "methylation" refers to the attachment of a methyl group (—$CH_3$) to another molecule. Typically, when DNA undergoes methylation, a methyl group is added to a cytosine bearing nucleotide, commonly at a CpG sequence, although methylation can occur at other sites as well. Proteins, such as, for example, histone 3, may also be methylated at a lysine, e.g., lysine 9.

The term "demethylation" refers to the removal of a methyl group (—$CH_3$) from another molecule. Typically, when DNA undergoes demethylation, a methyl group is removed from a cytosine bearing nucleotide, commonly at a CpG sequence, although demethylation can occur at other sites as well. Proteins, such as, for example, histone 3, may also be demethylated at a lysine, e.g., lysine 9.

The phrase "pharmaceutically acceptable carrier" refers to compositions that facilitate the introduction of dsRNA into a cell and includes but is not limited to solvents or dispersants, coatings, anti-infective agents, isotonic agents, agents that mediate absorption time or release of the inventive polynucleotides and double stranded polynucleotides. Examples of "pharmaceutically acceptable carriers" include liposomes that can be neutral or cationic, can also comprise molecules such as chloroquine and 1,2-dioleoyl-sn-glycero-3-phosphatidyle-thanolamine, which can help destabilize endosomes and thereby aid in delivery of liposome contents into a cell, including a cell's nucleus. Examples of other pharmaceutically acceptable carriers include poly-L-lysine, polyalkylcyanoacrylate nanoparticles, polyethyleneimines, and any suitable PAMAM dendrimers (polyamidoamine) known in the art with various cores such as, for example, ethylene-diamine cores, and various surface functional groups such as, for example, cationic and anionic functional groups, amines, ethanolamines, aminodecyl.

Overview

The present disclosure provides methods and compositions for activation of a NKX3-1 gene by introducing in the nucleus of a cell at least one small activating RNA (saRNA) molecule comprising at least a first ribonucleic acid strand comprising a sequence selected from SEQ ID NO: 1, SEQ ID NO: 2, SEQ ID NO: 3, and SEQ ID NO: 4, wherein the sequence is complementary to a sequence of the promoter region of the NKX3-1 gene and is sufficient to activate transcription of the NKX3-1 gene.

The present also disclosure provides methods and compositions for activation of a KLF4 gene by introducing in the nucleus of a cell at least one a small activating RNA (saRNA) molecule comprising at least a first ribonucleic acid strand comprising a sequence selected from SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, wherein the sequence is complementary to a promoter region sequence of a KLF4 gene and is sufficient to activate transcription of the KLF4 gene.

The saRNA molecule can be provided as a single stranded molecule. The saRNA molecule can also be provided as a double-stranded molecule, with a second strand complementary to the first strand and forming a duplex region with the first strand, usually with at least a two residue overhang at the 3' ends of each of the first and second strands. For example, the saRNA may be a double-stranded molecule comprising a first ribonucleic acid strand comprising a sequence from SEQ ID NO: 1, the second ribonucleic acid strand comprises a sequence from SEQ ID NO: 2.

The saRNA can also be provided as single stranded molecule that forms a double-stranded region with a hairpin loop, wherein a first sequence forming the double stranded region is a ribonucleotide sequence complementary to a promoter region sequence of the gene, and a second sequence forming the double strand comprises a ribonucleotide sequence complementary to the first sequence and forming a duplex region with the first region, usually with at least a two residue overhang at the 3' ends of the strand. For example, a single stranded saRNA may be made by joining the 3' end of the sequence of SEQ ID NO: 1 to the 5' end of the sequence of SEQ ID NO: 2 separated by a hairpin loop sequence, such as, AAU, AUAU, etc.

As described in the examples in more detail, the saRNA sequences targeting the NKX3-1 promoter induce NKX3-1 mRNA and protein expression in human cells. The activation of NKX3-1 mRNA and protein expression by saRNAs targeting the NKX3-1 promoter results in a decrease in cell viability of a number of prostate cancer cell lines and reduces tumor burden and mortality in prostate cancer mice models. Also disclosed are saRNA sequences targeting the KLF4 promoter induce KLF4 mRNA and protein expression in human cells. The activation of KLF4 mRNA and protein expression by saRNAs targeting the KLF4 promoter results in a decrease in cell viability of a number of prostate cancer cell lines.

In one aspect the disclosure provides methods of increasing expression of a NKX3-1 gene or KLF4 gene (i.e., gene activation) by introducing a saRNA molecule disclosed above into a mammalian cell (which can be accomplished by delivery of the saRNA into the cell directly or as a result of expression of the saRNA from a DNA introduced into the cell). The introduction results in an increase in expression of the target gene. Increasing NKX3-1 gene activity and KLF4 gene activity can be useful in many contexts, for example, inhibition of cellular proliferation, inhibition of cellular transformation and inhibition of cellular migration (e.g., as an anti-cancer agent). In another aspect, the disclosure provides compositions and pharmaceutical preparations comprising at least one saRNA molecule.

These and other aspects of saRNA targeting NKX3-1 gene and saRNA targeting KLF4 will now be described in more detail.

NKX3-1

NKX3-1, as used herein refers to the human NKX3-1 gene. NKX3-1, a homolog gene of *drosophila* NK-3, is a member of the NK subfamily of homeodomain-containing transcription factor genes (10) and is closely related to NK-2 and NK-4. It has an expression pattern largely restricted in the prostate in an androgen regulated manner (11). Human NKX3-1 encodes for at least 5 splice variants resulting in different open reading frames (ORFs) with deletions in the N-terminal region upstream of the homeobox domain (25). Although the functional role of this region is unknown, conserved motifs in this region of other closely related homeodomain proteins such as TN-domain in NK-2 may modulate the activity/function of the protein. (26). Thus, variant forms of NKX3.1 may have differential activities or functions, for example, this region may have a modulatory role in DNA binding by NKX3.1 (25). NKX3-1 is a prostate specific tumor suppressor gene. Functional inactivation of NKX3-1 has been strongly implicated in prostate cancer initiation, development, and progression to androgen-independent cancer.

KLF4

KLF4/GKLF (gut-enriched Krüpple-like factor) is a member of the Krüpple-like factor subfamily of zinc finger proteins. Upon binding to GC-rich SP1-like elements in gene promoters, KLF4 acts as a transcription regulator either activating or repressing gene expression depending on whether it interacts with co-activators (i.e. p300 and CBP) or co-repressors (i.e. HDAC3) (9). In cultured cells, KLF4 expression is associated with growth arrest processes including serum deprivation, contact inhibition, and DNA damage (10). KLF4 may act as a negative regulator of cell growth.

The role of KLF4 in the prostate cancer etiology has never been examined. As disclosed herein, KLF4 is downregulated in all prostate cancer cell lines and in prostate cancer tissues.

Compositions

As noted above the present disclosure provides short activating RNA (saRNA) molecules for use in performing NKX3-1 gene activation (e.g., increase gene expression) in mammalian cells by targeting a region of the promoter sequence of the NKX3-1 gene. Also provided are short activating RNA (saRNA) molecules for use in performing KLF4 gene activation (e.g., increase gene expression) in mammalian cells by targeting a region of the promoter sequence of the KLF4 gene.

A composition for activating NKX3-1 gene may comprise a saRNA molecule comprising at least one of a first ribonucleic acid strand comprising a ribonucleotide sequence selected from: SEQ ID NO: 1, 2, 3, and 4. A composition for activating NKX3-1 gene may comprise two or more saRNA molecules, where each saRNA molecule comprises a ribonucleic acid strand comprising a sequence of different SEQ ID NOs provided herein. For example, a composition comprising a mixture of two or more different NKX3-1 saRNA is also contemplated. Compositions comprising two or more first ribonucleic acid strands comprising a ribonucleotide sequence complementary to different regions of the same target promoter sequence (e.g., different NKX3-1 saRNA) may enhance the activation of the target gene.

A composition for activating a KLF4 gene may comprise a small activating RNA (saRNA) molecule comprising at least a first ribonucleic acid strand comprising a sequence selected from SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, wherein the sequence is complementary to a promoter region sequence of a KLF4 gene and is sufficient to activate transcription of the KLF4 gene. In certain aspects, the saRNA molecule may comprise a second ribonucleic acid strand, wherein when the first ribonucleic acid strand comprises a sequence from SEQ ID NO: 5, the second ribonucleic acid strand comprises a sequence from SEQ ID NO: 6, when the first ribonucleic acid strand comprises a sequence from SEQ ID NO: 7, the second ribonucleic acid strand comprises a sequence from SEQ ID NO: 8, and when the first ribonucleic acid strand comprises a sequence from SEQ ID NO: 9, the second ribonucleic acid strand comprises a sequence from SEQ ID NO: 10.

In certain embodiments, the composition may comprise at least one saRNA molecule comprising a ribonucleic acid comprising a sequence selected from the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. In certain embodiments, the composition may comprise at least one saRNA molecule comprising a ribonucleic acid comprising a sequence having at least 99%, 95%, 90%, 85%, or less sequence identity to a sequence selected from the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. In certain embodiments, the composition may comprise two or more saRNA molecules, where the ribonucleic acid strand(s) of each saRNA is complementary to a different sequence within the promoter region of the target gene (e.g., NKX3-1 gene or KLF4 gene). In certain embodiments, the composition may comprise two or more saRNA molecules, where the ribonucleic acid strand(s) of each saRNA is complementary to different sequences within the promoter regions of two target genes (e.g., NKX3-1 gene and KLF4 gene).

The saRNA molecules may comprise moieties other than ribonucleotide moieties, including, but not limited to, modified nucleotides, modified internucleotide linkages, non-nucleotides, deoxynucleotides and analogs of the aforementioned nucleotides.

saRNAs compounds of the present invention can be duplexes, and can be composed of separate strands or can comprise of a single strand of RNA that forms short hairpin dsRNAs with a hairpin loop as long as, for example, about 3 to about 23 or more nucleotides, about 5 to about 22, about 6 to about 21, about 7 to about 20, about 8 to about 19, about 9 to about 18, about 10 to about 17, about 11 to about 16, about 12 to about 15, about 13 to about 14 nucleotides, such as 3, or 4, or 5, or 7, or 12, or 18, or 21 nucleotides. RNAs having loops or hairpin loops can include structures where the loops are connected to the stem by linkers such as flexible linkers. Flexible linkers can be selected of a wide variety of chemical structures, as long as they are of sufficient length and materials to enable effective intramolecular hybridization of the stem elements.

Although the sequences in the SEQ ID NOs disclosed herein are perfectly complementary to a region in the promoter sequence of the target gene, in some embodiments, the ribonucleotide strand may comprise a sequence that is less than 100% complementary to a sequence in the promoter region of the target gene, including about 99% complementary, 98% complementary, 97% complementary, 96% complementary, 95% complementary, 94% complementary, 93% complementary, 92% complementary, 91% complementary, 90% complementary, 85% complementary, 80% complementary, 75% complementary, 70% complementary to the promoter region of the target gene.

The nucleotides of the saRNA, or at least one strand of a duplex saRNA, may be modified so as to provide a desired characteristic. For example, the saRNA molecules of the invention can comprise modification of a naturally occurring or non-naturally occurring polynucleotide that provides for enhanced nuclear uptake. An example of a nuclear uptake enhancing modification is a stabilizing modification, such as a modified internucleotide linkage, that confers sufficient stability on a molecule, such as a nucleic acid, to render it sufficiently resistant to degradation (e.g., by nucleases) such that the associated nucleic acid can accumulate in the nucleus of a cell when exogenously introduced into the cell. In this example, entry into the cell's nucleus is facilitated by the ability of the modified nucleic acid to resist nucleases sufficiently well such that an effective concentration of the nucleic acid can be achieved inside the nucleus.

Furthermore, the saRNA can be 2'-O-bis(2-hydroxyethoxy)methyl orthoester modified to provide for stability of the ribonucleic acid molecule. Other modification, include, for example a backbone phosphate group modification (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of the saRNA. Phosphorothioates and phosphorodithioates are more resistant to degradation in vivo than their unmodified oligonucleotide counterparts, increasing the half-lives of the saRNA making them more available to the subject being treated. A saRNA may also be modified to comprise N3'-P5' (NP) phosphoramidate, morpholino phosphorociamidate (MF), locked nucleic acid (LNA), 2'-O-methoxyethyl (MOE), or 2'-fluoro, arabino-nucleic acid (FANA), which can enhance the resistance of the polynucleotide to nuclease degradation (see, e.g., Faria et al. (2001) *Nature Biotechnol.* 19:40-44; Toulme (2001) *Nature Biotechnol.* 19:17-18).

The saRNA may be synthesized by any method that is now known or that comes to be known for synthesizing saRNA molecules and that from reading this disclosure, one skilled in the art would conclude would be useful in connection with the present invention. For example, one may use methods of chemical synthesis such as methods that employ Dharmacon, Inc.'s proprietary ACE® technology. Alternatively, one could also use template dependant synthesis methods. Synthesis may be carried out using modified or non-modified, natural or non-natural bases as disclosed herein. Moreover, synthesis may be carried out with or without modified or non-modified nucleic acid backbone as disclosed herein.

In addition, the saRNA molecules may be synthesized in a host cell by any method that is now known or that comes to be known for synthesizing saRNA molecules in a host cell. For example, saRNA molecules can be expressed from recombinant circular or linear DNA vector using any suitable promoter. Suitable promoters for expressing saRNA molecules of the invention from a vector include, for example, the U6 or H1 RNA pol III promoter sequences and the cytomegalovirus promoter. Selection of other suitable promoters is within the skill in the art. Suitable vectors for use with the subject invention include those described in U.S. Pat. No. 5,624,803, the disclosure of which is incorporated herein in its entirely. The recombinant plasmids of the invention can also comprise inducible or regulatable promoters for expression of the saRNA molecule in a particular tissue or in a particular intracellular environment.

The saRNA molecules of the invention can be expressed from a recombinant nucleic acid vector either as two separate, complementary RNA molecules, or as a single RNA molecule with two complementary regions. Selection of vectors suitable for expressing saRNA of the invention, methods for inserting nucleic acid sequences for expressing the saRNA into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference. Other methods for delivery and intracellular expression suitable for use in the invention are described in, for example, U.S. Patent Application Publication Nos. 20040005593, 20050048647, 20050060771, the entire disclosures of which are herein incorporated by reference.

Once synthesized, the polynucleotides of the present invention may immediately be used or be stored for future use. In some embodiments, the polynucleotides of the invention are stored as duplexes in a suitable buffer. Many buffers are known in the art suitable for storing saRNAs. For example, the buffer may be comprised of 100 mM KCl, 30 mM HEPES-pH 7.5, and 1 mM $MgCl_2$. In representative embodiments, the double stranded polynucleotides of the present invention retain 30% to 100% of their activity when stored in such a buffer at 4° C. for one year. More preferably, they retain 80% to 100% of their biological activity when stored in such a buffer at 4° C. for one year. Alternatively, the compositions can be stored at −20° C. in such a buffer for at least a year or more. Usually, storage for a year or more at −20° C. results in less than a 50% decrease in biological activity. More usually, storage for a year or more at −20° C. results in less than a 20% decrease in biological activity after a year or more. Furthermore, storage for a year or more at −20° C. results in less than a 10% decrease in biological activity.

In order to ensure stability of the saRNA prior to usage, they may be retained in dry form (e.g., lyophilized form) at −20° C. until they are ready for use. Prior to usage, they should be resuspended; however, even once resuspended, for example, in the aforementioned buffer, they should be kept at −20° C. until used. The aforementioned buffer, prior to use, may be stored at approximately 4° C. or room temperature. Effective temperatures at which to conduct transfection are well known to persons skilled in the art, but include for example, room temperature.

Methods

The present disclosure provides methods of increasing NKX3-1 gene expression comprising introducing a saRNA molecule disclosed above into a mammalian cell's nucleus, wherein the saRNA molecule has a strand that is complementary to a region of promoter sequence of the NKX3-1 gene, wherein the introduction results in an increase in expression of the NKX3-1 gene. The present disclosure also provides methods of increasing KLF4 gene expression comprising introducing a saRNA molecule disclosed above into a mammalian cell's nucleus, wherein the saRNA molecule has a strand that is complementary to a region of promoter sequence of the KLF4 gene, wherein the introduction results in an increase in expression of the KLF4 gene.

In general, the methods of the present invention are carried out by contacting a cell with an saRNA molecule disclosed, wherein the introduction results in an increase in expression of the gene.

In representative embodiments, an increase in NKX3-1 or KLF4 gene expression results in at least about a 2-fold increase or more in transcription associated with NKX3-1 or KLF4 gene sequence, as compared to a control, e.g., in the absence of the saRNA molecule. In some embodiments, the increase in NKX3-1 or KLF4 gene expression results in at least about a 2.5-fold increase or more, at least about a 3-fold increase or more, at least about a 3.5-fold increase or more, at least about a 4-fold increase or more, at least about a 4.5-fold increase or more, at least about a 5-fold increase or more, at least about a 5.5-fold increase or more, at least about a 6-fold increase or more, at least about a 6.5-fold increase or more, at least about a 7-fold increase or more, at least about a 7.5-fold increase or more at least about a 8-fold increase or more, and up to about 10-fold increase or more, including about 15-fold increase or more, about 20-fold increase or more, such as 25-fold increase or more. An increase in NKX3-1 or KLF4 gene expression or activity can be measured by any of a variety of methods well known in the art. Suitable methods of examining gene expression or activity include measuring target gene nucleic acid transcription level, target gene mRNA level, target gene protein level, for example.

Because the ability of the modified dsRNAs of the present invention to retain functionality and resist degradation of the compound is not dependent on the sequence of the bases, the cell type, or the species into which it is introduced, the present invention is applicable across a broad range of mammals, including but not limited to humans. The present invention is particularly advantageous for use in mammals such as cattle, horse, goats, pigs, sheep, canines, rodents such as hamsters, mice, and rats, and primates such as, for example, gorillas, chimpanzees, and humans. Transgenic mammals may also be used, e.g. mammals that have a chimeric gene sequence. Methods of making transgenic animals are well known in the art, see, for example, U.S. Pat. No. 5,614,396.

The present invention may be used advantageously with diverse cell types including those of the germ cell line, as well as somatic cells. The cells may be stem cells or differentiated cells. For example, the cell types may be embryonic cells, oocytes sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

The compositions and methods of the present invention may be administered to a cell or applied by any method that is now known or that comes to be known and that from reading this disclosure, one skilled in the art would conclude would be useful with the present invention. For example, the polynucleotides may be passively delivered to cells.

Passive uptake of modified polynucleotides can be modulated, for example, by the presence of a conjugate such as a polyethylene glycol moiety or a cholesterol moiety at the 5' terminal of the sense strand and/or, in appropriate circumstances, a pharmaceutically acceptable carrier.

The saRNA may be delivered to a cell by any method that is now known or that comes to be known and that from reading this disclosure, persons skilled in the art would determine would be useful in connection with the present invention in enabling saRNA to cross the cellular membrane and/or the nuclear membrane. These methods include, but are not limited to, any manner of transfection, such as for example transfection employing DEAE-Dextran, calcium phosphate, cationic lipids/liposomes, micelles, manipulation of pressure, microinjection, electroporation, immunoporation, use of vectors such as viruses (e.g., RNA virus), plasmids, cell fusions, and coupling of the polynucleotides to specific conjugates or ligands such as antibodies, antigens, or receptors, passive introduction, adding moieties to the saRNA that facilitate its uptake, and the like.

The dsRNAs of the present invention may be used in a diverse set of applications involving activation of the target gene, including but not limited to basic research, drug discovery and development, diagnostics and therapeutics. For example, the present invention may be used to validate whether a gene product is a target for drug discovery or development. In this application, a target nucleic acid sequence of interest is identified for activation (e.g., increasing expression). For example, a cell is contacted with a saRNA specific for targeting the regulatory sequence of the particular target sequence of interest. The cell is maintained under conditions allowing for the methylation of the targeted DNA and/or methylation of nuclear proteins such as, for example, one or more histones, resulting in decreased activity or transcription of a gene. The extent of any increased activity, such as, for example, transcription or translation, of the gene is then assessed, along with the effect of such increased activity, and a determination is made that if activity is increased, then the nucleic acid sequence of interest is a target for drug discovery or development. In this manner, phenotypically desirable effects can be associated with saRNA activation of particular target nucleic acids of interest, and in appropriate cases toxicity and pharmacokinetic studies can be undertaken and therapeutic preparations developed.

Still further, the present invention may be used in applications, such as diagnostics, prophylactics, and therapeutics. For these applications, an organism suspected of having a disease or disorder that is amenable to modulation by manipulation of a particular target nucleic acid of interest is treated by administering saRNA. Results of the saRNA treatment may be ameliorative, palliative, prophylactic, and/or diagnostic of a particular disease or disorder. In representative embodiments, the saRNA is administered in a pharmaceutically acceptable manner with a pharmaceutically acceptable carrier with or without a diluent.

Subjects suitable for treatment with a method of the present invention involving saRNAs include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but are not limited to, abnormal stimulation of endothelial cells (e.g., atherosclerosis), solid tumors and tumor metastasis, benign tumors, for example, porstate cancer, gastrointestinal cancer, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neuroscular glaucoma and Oster Webber syndrome, psoriasis, restinosis, fungal, parasitic and viral infections such as cytomegaloviral infections. In certain cases, a saRNA molecule that activates NKX3-1 gene may be used simultaneously (for example, in a single composition or as separate compositions that are administered simultaneously) with a saRNA molecule that activates KLF4 gene. Such a simultaneous use of two saRNA targeting two different genes may be applicable to treatment of cell proliferative diseases, such as cancer, for example, prostate cancer, gastrointestinal cancer. Subjects to be treated according to the methods of the invention include any individual having any of the above-mentioned disorders.

The invention should not be construed to be limited solely to the treatment of patients having a cellular proliferative disease. Rather, the invention should be construed to include the treatment of patients having conditions or disease associated with decreased expression of NKX3-1 gene and or KLF4 gene that would benefit from the methods of the subject invention.

Such subjects may be tested in order to assay the activity and efficacy of the subject saRNAs. Significant improvements in one or more of parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like).

Pharmaceutical Preparations Containing saRNA Molecules

Also provided by the invention are pharmaceutical preparations of the subject saRNA molecules described above. The subject saRNA compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols, in a sterile vial or in a syringe. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc. The administration can be systemic or localized delivery of the formulation to a site in need of treatment, e.g., localized delivery to a tumor.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms of the saRNA Molecules

In pharmaceutical dosage forms, the subject saRNA molecules of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject saRNA compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, intravenous routes, i.e., any route of administration other than through the alimentary canal, and local injection, with intra or perituomoral injection being of interest, especially where a tumor is a solid or semi-solid tumor (e.g., Hodgkins lymphoma, non-Hodgkins lymphoma, and the like). Local injection into a tissue defining a biological compartment (e.g., prostate, ovary, regions of the heart (e.g., pericardial space defined by the pericardial sac), intrathecal space, synovial space, and the like) is also of interest. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject saRNA compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol, collagen, cholesterol; and if desired, with conventional additives such as solubilizers, isotonic agents, suspending agents, emulsifying agents, stabilizers and preservatives.

The saRNA compounds can also be delivered to the subject by enteral administration. Enteral routes of administration include, but are not necessarily limited to, oral and rectal (e.g., using a suppository) delivery.

Furthermore, the subject saRNA compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the saRNA Molecules

Depending on the subject and condition being treated and on the administration route, the subject saRNA molecules may be administered in dosages of, for example, 0.1 μg to 100 mg/kg body weight per day. In certain embodiments, the therapeutic administration is repeated until a desired effect is achieved. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Dosages for a given compound are readily determinable by those of skill in the art by a variety of means.

Although the dosage used will vary depending on the clinical goals to be achieved, a suitable dosage range is one which provides up to about 1 μg to about 1,000 μg or about 10,000 μg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject molceulces may be formulated with or otherwise administered in combination with other pharmaceutically active agents, including other agents that activate or suppress a biochemical activity, such as a chemotherapeutic agent. The subject compounds may be used to provide an increase in the effectiveness of another chemical, such as a pharmaceutical, or a decrease in the amount of another chemical, such as a pharmaceutical that is necessary to produce the desired biological effect.

Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

Furthermore, the saRNA compounds of the present invention may also be used in combination therapy with siRNA molecules. In such embodiments, the saRNA molecules may be administered to increase activation of a first gene and the siRNA molecule may be administered to silence expression of a second gene. For example, the saRNA molecules may be administered to increase activation of a tumor suppressor gene and the siRNA molecule may be administered to silence expression of an oncogene.

The saRNA molecules described herein may be used in combination therapy with other saRNA molecules. In one embodiment, a first saRNA molecule targeting a first sequence in a promoter region sequence of a first gene and a second saRNA molecule targeting a second sequence in the promoter region sequence of the first gene may be administered to increase activation of a first gene. In another embodiment, a first saRNA molecule may be administered to increase activation of a first gene (e.g. NKX3-1 gene) and a second siRNA molecule may be administered to increase activation of a second gene (e.g., KLF4 gene).

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject saRNA molecules, usually in oral or injectable doses, are provided. In such kits, in addition to the containers containing the unit doses will be an informational package insert describing the use and attendant benefits of the drugs in treating pathological condition of interest. Representative compounds and unit doses are those described herein above.

In one embodiment, the kit comprises a saRNA formulation in a sterile vial or in a syringe, which formulation can be suitable for injection in a mammal, particularly a human.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials were used in the examples 1-8.

saRNA Design and Synthesis saRNAs (also referred to as dsRNA) were designed and synthesized as previously described (1, 4). A dsRNA targeting the NKX3-1 promoter at position −360 and −381 relative to the transcription start site were designed. A dsRNA lacking significant homology to all known human sequences (dsControl) was utilized as a non-specific control.

The saRNA sequences are described blow.
saNKX3-1-381:

Sense:
(SEQ ID NO: 1)
5'-GAC GGU CCU GAA GAG CUA A [dT][dT]-3'

Antisense:
(SEQ ID NO: 2)
5'-UUA GCU CUU CAG GAC CGU C [dT][dT]-3' saNKX3-1-360:

Sense:
(SEQ ID NO: 3)
5'-GAC UGU UUG UCU UGA UCG U [dT][dT]-3'

Antisense:
(SEQ ID NO: 4)
5'-ACG AUC AAG ACA AAC AGU C [dT][dT]-3'

Cell Culture and Transfection

Human prostate cancer cell lines were grown in their respective growth medium containing 10% FBS, penicillin (100 U/ml) and streptomycin (100 µg/ml). The day before transfection, cells were plated in growth medium without antibiotics at a density of 50-60%. dsRNA was transfected at a concentration of 50 nM using RNAiMax (Invitrogen, Carlsbad, Calif.) according to the manufacturer's instructions.

Nucleic Acid Extraction

Total cellular RNA was isolated using the RNeasy Mini Kit (Qiagen, Valencia, Calif.). One microgram of RNA was used for cDNA synthesis using the ThermoScript™ RT-PCR system (Invitrogen). The resulting cDNA was amplified by PCR using gene specific primers.

Western Analysis

Cells were washed with PBS and lysed in RIPA buffer (50 mM Tris, pH 7.4, 150 mM NaCl, 1% Triton X-100, 0.5% deoxycholate, 0.1% SDS) with protease and phosphatase inhibitor cocktail for 15 min at 4° C. Lysates were clarified by centrifugation and supernatants were collected. Protein concentration was determined by using a BCA protein assay kit (Thermo Scientific, Waltham, Mass.). Proteins were resolved on SDS-PAGE gels and transferred to nitrocellulose membranes. The resulting blots were blocked with 5% non-fat dry milk and specific proteins were detected with primary antibodies. Blots were subsequently incubated with appropriate HRP-conjugated secondary antibodies and antigen-antibody complexes were visualized by chemiluminescence (Thermo Scientific).

Clonogenic Survival Assay

Exponentially growing cells were seeded in 12-well plates and reverse transfected with 25 nM saRNA using Lipofectamine RNAiMax. After 24 hrs, the transfected cells were harvested and seeded in 6-well plates at a density of 2000 cells/well. Culture medium without antibiotics was changed every 3 days. Colony formation was analyzed at day 12 by staining cells with crystal violet.

Cell Proliferation Assay

Cell proliferation was investigated using the CellTiter 96® AQueous One Solution Cell Proliferation Assay kit (Promega, Madison, Wis.). Transfection of dsRNA was carried out using Lipofectamine 2000 (Invitrogen) by following the reverse transfection protocol provided with the product. Briefly, transfection mixtures were prepared and added to each well of a 96-well plate. Cells were then subcultured into the wells containing the transfection mixtures at a density of 2×104 cells/ml in complete media without antibiotics. The plates were then incubated for 1-6 day. At end of the incubation period, 20 µl of CellTiter 96® AQueous One Solution was added to each well. After 1 hour, absorbance was measured on an ELISA plate reader (Bio-Tek Instruments Inc, Winooski, Vt.) at 490 nm.

In Vivo Study

Thirty athymic nude, homozygous male mice (nu/nu) at the age of 4 weeks were purchased from Simonsen Laboratories, Inc. After 5 days of acclimatization period, a total of $6.0 \times 10^6$ PC-3 cells were inoculated subcutaneously (s.c.) in 0.2 ml of PBS mixed with Matrigel through a 27-gauge needle into the lower flank of the mice. After 1 weeks when tumors reached an average weight of 0.28 g, the tumor-bearing mice were randomly divided into 3 treatment groups with one treated with PBS, one dsControl and one dsNKX3-1-381. All dsRNAs are formulated in SNALP by Alnylam Pharmaceuticals, Inc. The formulated dsRNA was injected into tumor using a gauge-30 needle. The dsRNA injection was repeated every 3 days for a total 3 times. Mice body weight and tumor size were recorded every 3 days. Mice were removed from the study upon reaching predetermined endpoint criteria and recorded as a study death. The endpoint criteria were as follows: (1) Single (right or left) flank tumor volume ≥1.5 cm³; (2) Body condition score (BCS) of −2 or less; (3) Weight loss of ≥20% from high body weight; (4) Active ulceration of tumor; (5) Illness and/or observed depression. At day 108 following the initial treatment, all mice were sacrificed and tumors were removed and weighted. Tumor weight in gram was calculated by the formula: weight=(width)²×length/2.

Example 1

Identification of a potent NKX3-1 saRNA

Bioinformatics analysis of human NKX3-1 promoter revealed that it contains a 188-bp CpG island which extends into the first exon of NKX3-1 gene and a typical TATA box exists at the −30 location relative to the transcription start site (TSS). By following rules derived from previous studies (1, 4), two 21-nt saRNAs targeting the human NKX3-1 promoter at locations −360 (dsNKX3-1-360) and −381 (dsNKX3-1-381) relative to the TSS were designed. These two saRNAs were transfected into 7 prostate cancer cell lines, LNCaP, CWR22R, PC-3, CWR22RV1, DuPro, LAPC-4 and DU145, at a concentration of 50 nM and NKX3-1 expression was analyzed 96 hours later. As shown in FIG. 1, NKX3-1 mRNA expression was induced by saNKX3-1-360 (also referred to as dsNKX3-1-360) in LNCaP, PC-3 and LAPC-4 cells, and by sadsNKX3-1-381 (also referred to as dsNKX3-1-381) in all cell lines with induction ranging from 1.5 (DU145) to 6.4 (LAPC-4) fold. The observation that saRNAs targeting different locations in a target gene induce the expression of the same target gene suggests that NKX3-1 activation results from sequence specific effect rather than a non-specific off-target effect. In the subsequent experiments, the more potent saRNA, dsNKX3-1-381 was used.

Example 2

Activation of NKX3-1 by saNKX3-1-381 in Different Prostate Cancer Cell Lines

Figure 2:
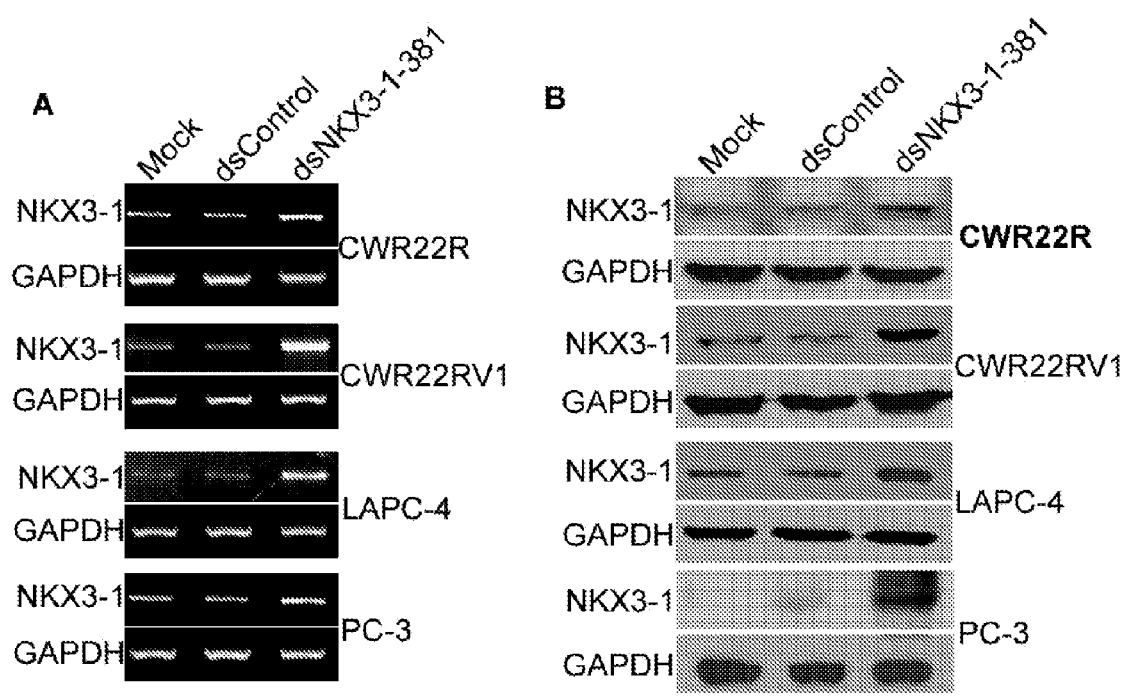
FIG. 2, panel A depicts mRNA expression levels of NKX3-1 and GAPDH assayed by RT-PCR in mock transfected, dsRNA control transfected, and dsNKX3-1-381 transfected cells. Panel B depicts results of a Western blot assay to detect NKX3-1 and GAPDH protein expression. The different cell lines tested are indicated.

To further validate the RT-PCR data, dsNKX3-1-381 was transfected into PC-3, CRW22R, CRW22RV1 and LAPC-4 cells, and both mRNA and protein expression were evaluated by semi-quantitative RT-PCR and Western blotting assay, respectively. As shown in FIG. 2, NKX3-1 expression was consistently induced at both mRNA and protein levels in all cell lines, even in PC-3 cells which do not express NKX3-1 protein at a detectable level.

Example 3

NKX3-1 Activation Inhibited Cell Proliferation and Survival In Vitro

Figure 3:
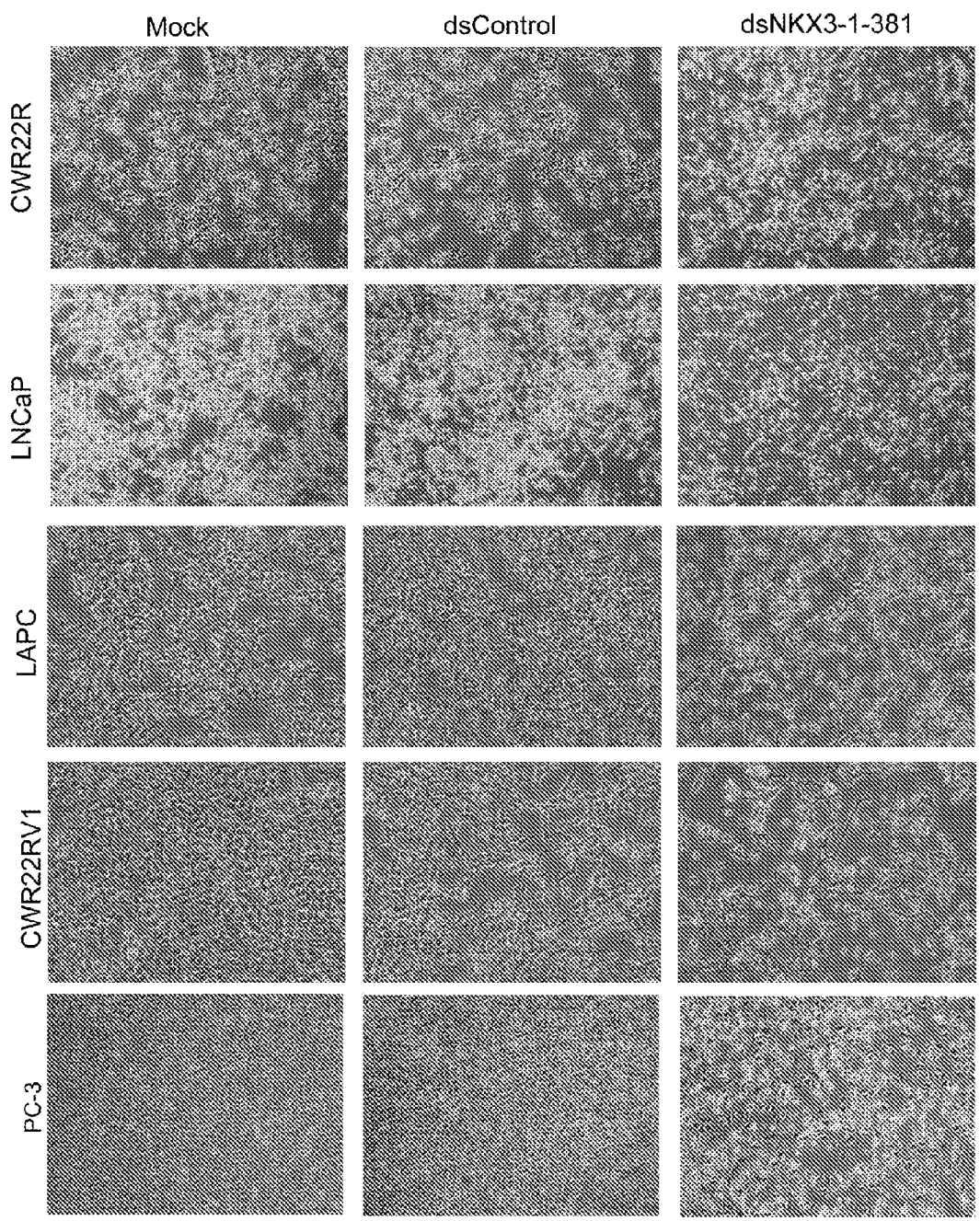
FIG. 3 depicts the anti-growth effect of dsNKX3-1-381 transfection on prostate cancer cells. Cells were transfected with 50 nM of the indicated dsRNA or mock transfected using RNAiMax (Invitrogen). Phase contrast cell images were taken at 96 hrs following transfection (40×).
Figure 4:
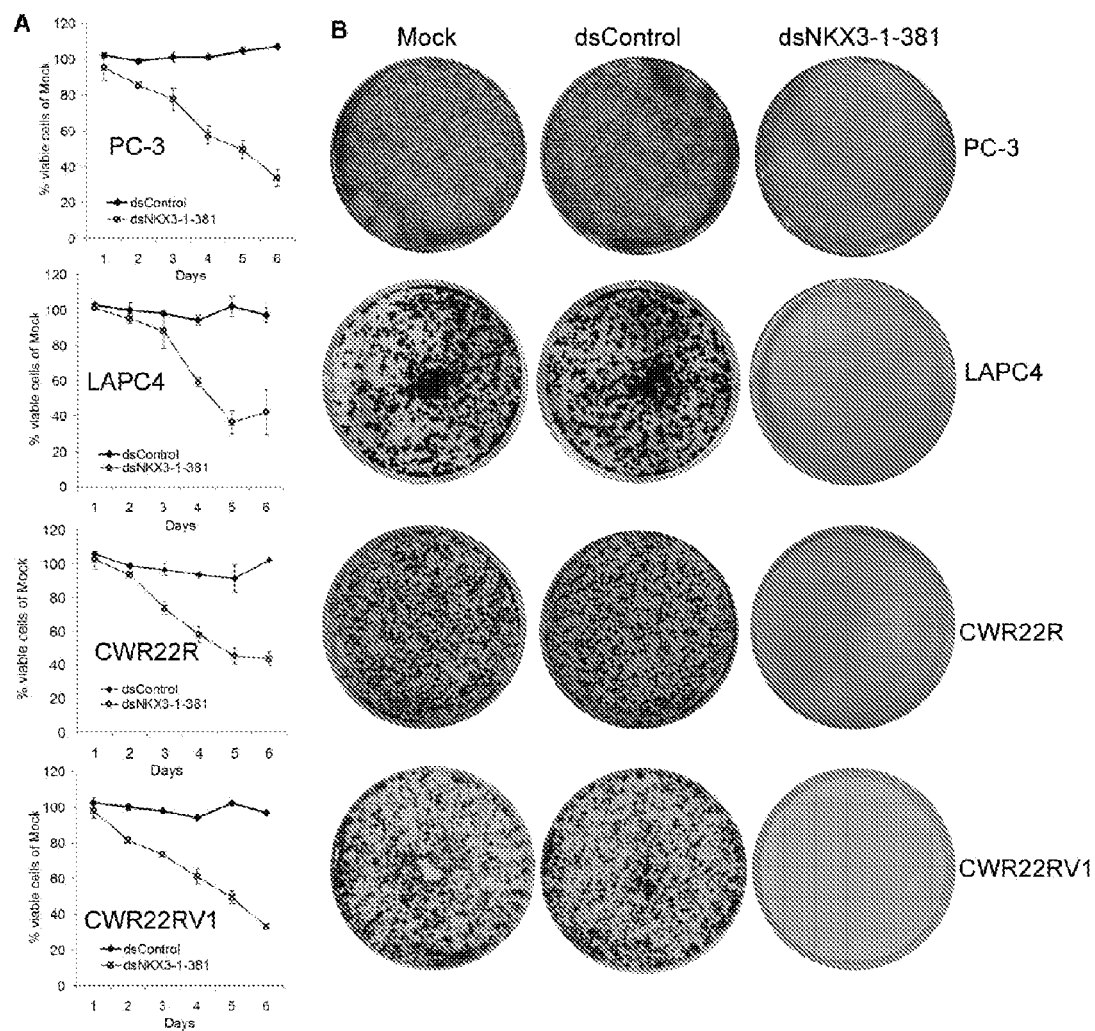
FIG. 4, panel A depicts percent of viable cells after transfection with ds control or dsNKX3-1-381. The results are plotted as the mean±SEM of two independent experiments relative to mock transfections. Panel B depicts that no colonies were detected in dsNKX3-1381 transfected LAPC4, CWR22R and CWR22RV1 cells on day 12 after transfection.

NKX3-1 is a known prostate specific tumor suppressor gene. Ectopic overexpression of NKX3-1 has been shown to inhibit PCa cell proliferation in vitro and tumor growth in nude mice (10, 27). All prostate cancer cells transfected with dsNKX3-1-381 displayed a phenotype of inhibited proliferation and increased cell death compared to mock or control dsRNA transfected cells (FIG. 3). To quantatively measure the inhibitory effect of dsNKX3-1-381 on cell proliferation, cell proliferation assays were performed. As shown in FIG. 4, panel A, a dramatic inhibition of cell proliferation was observed from day 2 to day 6 in all cell lines regardless of existing NKX3-1 expression levels. For PC-3, LAPC4, CWR22R and CWR22RV1 cells, dsNKX3-1-381 caused 66%, 58%, 56% and 67% inhibition, respectively, compared to mock transfection, while control dsRNA transfection had no significant effect on cell proliferation. To further evaluate how NKX3-1 activation may affect cell survival, colony formation assay was performed on these cell lines. In LAPC4, CWR22R and CWR22RV1 cells, a single transfection of dsNKX3-1-381 completely abolished colony formation by these cells, while ability to form colony growth was significantly decreased in PC-3 cells by dsNKX3-1-381 (FIG. 4, panel B). These results indicate that NKX3-1 activation by dsNKX3-1-381 can significantly inhibit cell proliferation and survival regardless of endogenous NKX3-1 expression.

Example 4

Induction of P21 and P27, and Downregulation of VEGFC by NKX3-1 Activation

Figure 5:
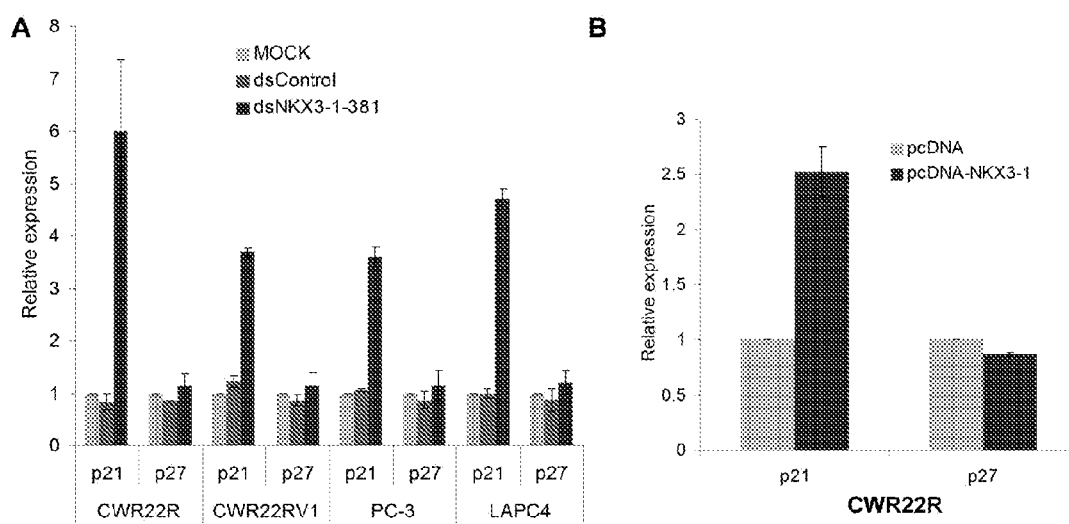
FIG. 5 depicts upregulation of p21 mRNA by saRNA-mediated NKX3-1 activation and vector-based NKX3-1 overexpression. Panel A depicts mRNA expression of p21 and p27 assessed by qRT-PCR at 96 hrs following transfection with mock (first bar from left), ds control (second bar from left), and dsNKX3-1-381 (third bar from left) for each of the cell lines indicated. Results are means±SD of two independent experiments. Panel B depicts mRNA expression of p21 and p27 in CWR22R cells transfected with pcDNA empty vector or pcDNA vector expressing NKX3-1 gene (pcDNA-NKX3-1).
Figure 6:
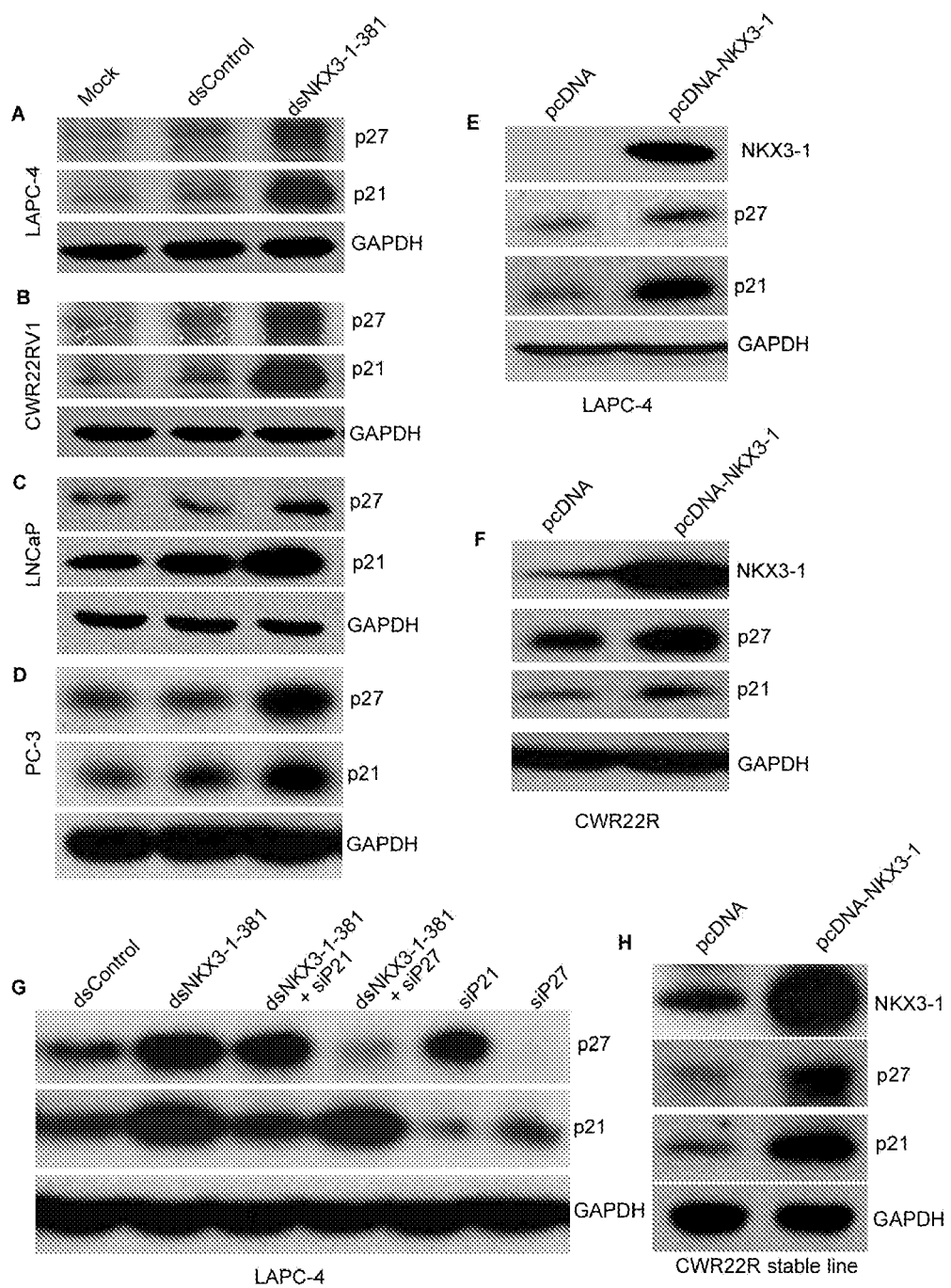
FIG. 6 depicts upregulation of p21 and p27 proteins by saRNA-mediated NKX3-1 activation and vector-based NKX3-1 overexpression. Panels A-D depict Western blots showing expression of p21 and p27 proteins in the cell lines indicated. Panels E and F show expression of NKX3-1, p21, p27, and GAPDH proteins in LAPC-4 and CWR22R cells, respectively, that were transiently transfected with pcDNA or pcDNA-NKX3-13-1 vectors. Panel G is a Western blot showing protein expression for p27, p21 and GAPDH in LAPC-4 cells transfected with the indicated dsRNAs for 96 hrs. Panel H is a Western blot showing protein expression for p27, p21 and GAPDH in CWR22R cells transfected with pcDNA empty vector or pcDNA vector expressing NKX3-1 gene (pcDNA-NKX3-1).

NKX3-1 is a transcription factor known to bind to the consensus sequence "TAAGTA" (28), to also bind to canonical "TAAT" sites and Nkx2.1 site "CAAGTG" albeit with weaker affinity (29). A cDNA expression profiling in PC-3 cells overexpressing NKX3-1 showed that several cell cycle related genes are regulated by NKX3-1 (30). For example, p27 and p21 are upregulated and BCL2, ABCB1 are downregulated by NKX3-1 (30). To explore the molecular mechanisms that led to inhibited cell proliferation and survival following NKX3-1 activation, the expression of known NKX3-1 downstream genes including p21, p27 and VEGFC was evaluated. As shown in FIG. 5, panel A, transfection of dsNKX3-1-381 into different prostate cancer cells caused dramatic induction of p21 mRNA expression but had no apparent effect on p27 mRNA expression. To validate the results, stable NKX3-1 expressing lines from CWR22R cells were created. In CWR22R cells stably expressing NKX3-1 (pcDNA-NKX3-1), a 2.5 fold higher expression of p21 mRNA was detected compared to a stable line that carried an empty vector (pcDNA).

p21 and p27 protein expression in either dsRNA transfected cells or cells transfected with NKX3-1 expressing vectors was also evaluated. At protein level, both p21 and p27 was induced by dsNKX3-1-381 transfection (FIG. 6, panel A). Similarly, these results were validated in cells either transiently (FIG. 6, panels E and F) or stably (FIG. 6, panel H) expressing NKX3-1. To illustrate that the induction of p21 expression was independent of expression of p27 and vice versa, either p21 or p27 was knocked down using their respective siRNA. Knockdown of p21 did not affect p27 activation by dsNKX3-1-381 and vice versa (FIG. 6, panel G). Taken together, saRNA mediated NKX3-1 activation induces expression of p21 mRNA and protein. saRNA mediated NKX3-1 activation also induces p27 mRNA and protein expression. p21 and p27 expression may play a role in the observed inhibitory effects of NKX3-1 activation on cell proliferation and survival.

Figure 7:
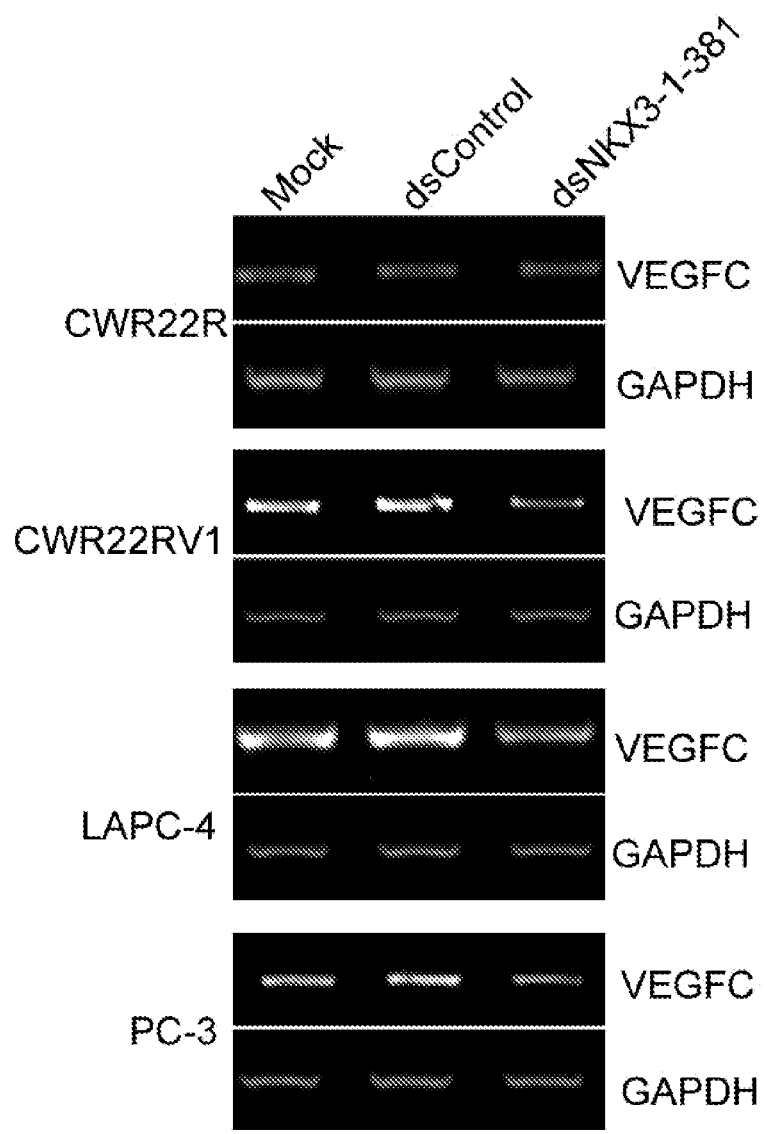
FIG. 7 depicts downregulation of VEGFC by saRNA mediated NKX3-1 activation. Cells were transfected with 50 nM of the indicated dsRNA or mock transfected. mRNA expression of VEGFC and GAPDH was assessed by semi-quantitative RT-PCR at 96 hrs following transfection.

It has been found that NKX3-1 can repress VEGF-C by directly binding to its promoter (31). Loss of NKX3-1 leads to increased VEGF-C expression and may result in lymphangiogenesis in late stages of advanced prostate cancer (31). Because VEGF family of proteins plays major roles in angiogenesis and lymphangiogenesis, and VEGF-C is mainly involved in lymphangiogenesis (32, 33), Zhang et al suggested that VEGF-C may facilitate prostate cancer metastasis to lymph nodes (31). In deed, overexpression of NKX3-1 in PC-3 cells significantly decreases the cells ability to survive and invade (30). In a microarray assay in PC-3 cells with ectopic expression of NKX3-1, several other genes related to cancer cell invasion are dramatically changed including matrix metalloproteinase-7 (MMP7), laminin alpha 4 (LAMA4), COL4A1, A5, 5A2, 6A1 and 7A1, PAI-I and IL1A (30). Taken together, activation of NKX3-1 may have beneficial effects on preventing and treating prostate cancer metastasis. The expression of VEGFC in prostate cancer cell lines transfected with dsNKX3-1-381 was evaluated. As shown in FIG. 7, downregulation of VEGF-C mRNA expression was evident in CWR22RV1, LAPC-4 and PC-3 cells transfected with dsNKX3-1-381, thus confirming VEGFC as a downstream target of NKX3-1

Example 5

NKX3-1 Suppresses ERK Transcription and Phosphorylation

Figure 8:
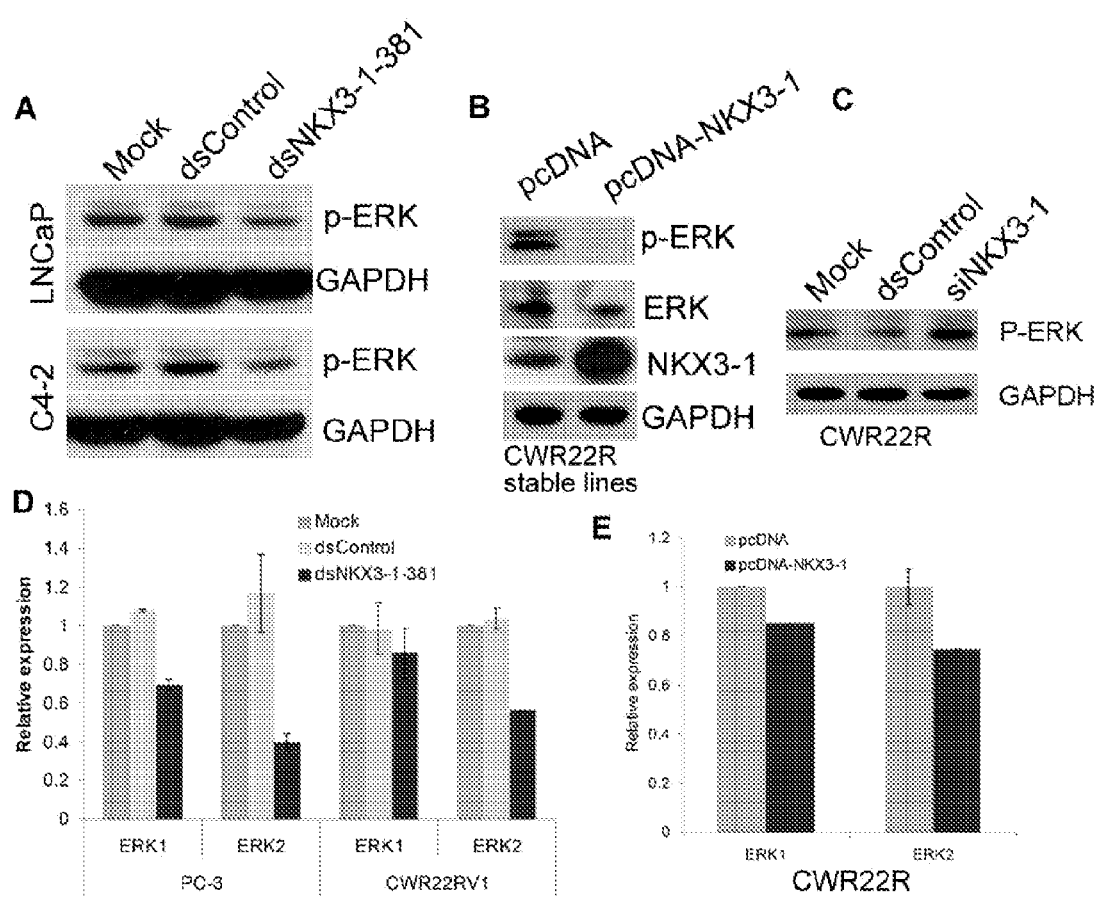
FIG. 8 shows that NKX3-1 suppresses ERK expression and phosphorylation. Panel A. Cells were transfected with 50 nM of the indicated dsRNA for 96 hrs. Phosphorylated ERK (p-ERK) was detected by Western blotting assays. Panel B, p-ERK and total ERK was detected in NKX3-1 expressing stable CWR22R cell lines. Panel C, CWR22R cells were transfected with the indicated dsRNA and p-ERK levels were detected by Western blotting assays. Panels D and E, ERK1 and ERK2 mRNA expression was analyzed by qRT-PCR in cells transfected with dsNKX3-1381 dsRNA and in CWR22R stable cell lines, respectively.

Extracellular signal-regulated kinase 1 and 2 (ERK1 and ERK2) signaling pathways are important for androgen-induced prostate morphogenesis and development (34-36) and mediates processes critical for the proliferation, apoptosis, invasion and metastasis of prostate cancer cells (37, 38) (39, 40). To investigate whether ERK signaling pathway mediates tumor suppressing effects of NKX3-1, ERK phosphorylation in cells with saRNA NKX3-1-381 or vector-mediated NKX3-1 overexpression or RNAi mediated NKX3-1 knockdown was evaluated. As shown in FIG. 8, panels A-C, phosphorylated ERK including ERK1 and ERK2 was significantly downregulated by NKX3-1 overexpression, while RNAi mediated NKX3-1 depletion induced ERK phosphorylation (FIG. 8, panel C). Interestingly, the level of total ERK was also affected in a similar way as p-ERK (FIG. 8, panel B) suggesting that ERK is regulated by NKX3-1 at the transcriptional level. In deed, analysis of ERK mRNA expression showed that both ERK1 and ERK2 were downregulated by NKX3-1 overexpression with the suppression on ERK2 being more prominent (FIG. 8, panels D and E).

Example 6

In Vivo Anti-Tumor Effect of NKX3-1 Activation Via saRNA

To test in vivo antitumor effects of NKX3-1 saRNA, xenograft prostate cancer models were treated with NKX3-1 saRNA. Tumor burden and animal survival were recorded as the primary end points.

Treatment Groups and Regimen.

A total of 32 nude mice received subcutaneous injection of $6 \times 10^6$ PC-3 cells at the right lower flank. After 7 days, 28 mice (93.3%) developed visible tumors with an average tumor weight of 0.28 g. These mice were randomly divided into 3 treatment groups (Table 1) and were administrated intratumorally with 150 μl PBS or 150 μl of the specified dsRNA (1 mg/ml) formulated in stable nucleic acid lipid particles (SNALPs). The treatment was repeated two more times on day 10 and 13. Mice were then monitored for tumor weight, body weight and body conditions. Mice were removed from the study upon reaching predetermined endpoint criteria and recorded as a study death. The endpoint criteria were as follows: (1) Single (right or left) flank tumor volume $\geq 1.5$ cm$^3$; (2) Body condition score (BCS) of −2 or less; (3) Weight loss of $\geq 20\%$ from high body weight; (4) Active ulceration of tumor; (5) Illness and/or observed depression.

TABLE 1

Animal groups and treatment regimen.

| Treatment group | Number of mice | Treatment |
|---|---|---|
| PBS | 9 | PBS 150 μl × 3 |
| dsControl | 10 | dsControl-UM-LNP01 (1 mg/ml) 150 μl × 3 |
| dsNKX3-1-381 | 9 | dsNKX3-1-381-UM-LNP01 (1 mg/ml) 150 μl × 3 |
| Total | 28 | |

Figure 9:
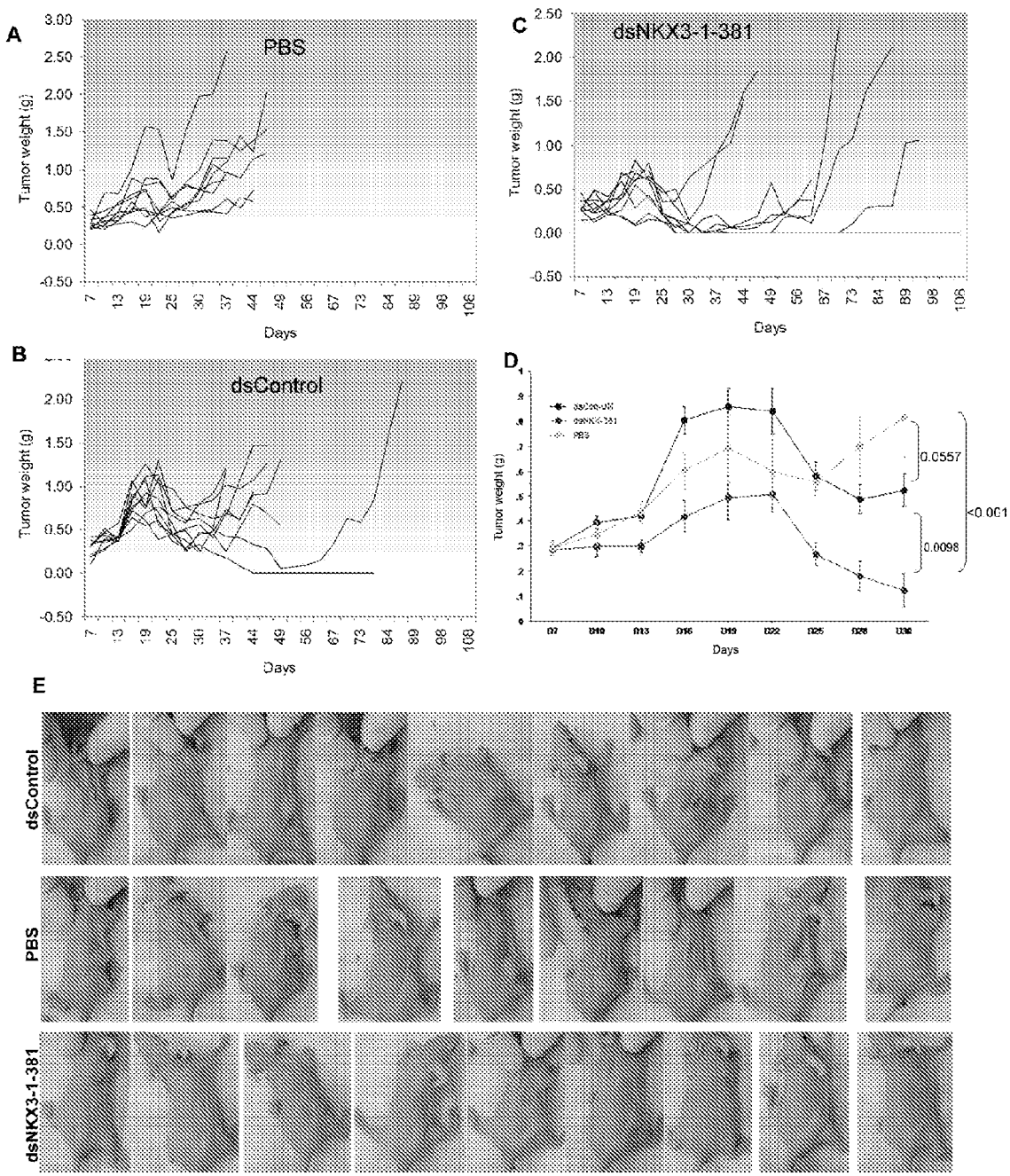
FIG. 9 shows that NKX3-1 saRNA decreases tumor burden. Panels A-C, tumor volume changes during the course of study. Tumor weight (g) at different time points was calculated by the formula [weight (g)=½ (length×width$^2$)]. Panel D, tumor weight measured before day 30 when all mice were in the study. Panel E, mouse pictures taken at day 28. Smaller tumor size and overall healthier condition of dsNKX3-1-381 mice were observed.

Results dsNKX3-1-381 treatment caused a significant reduction in tumor burden compared to PBS or control dsRNA treated tumors. At day 30 when all mice were surviving, the average tumor weight for dsNKX3-1-381 group was 0.18 g, a 74.2% (p=0.0002) and 63.1% (p=0.012) reduction compared to that for PBS (0.70 g) and dsControl (0.49 g), respectively (FIG. 9). At this time, three mice in the dsNKX3-1-381 treatment group were free of visible tumors.

Figure 10:
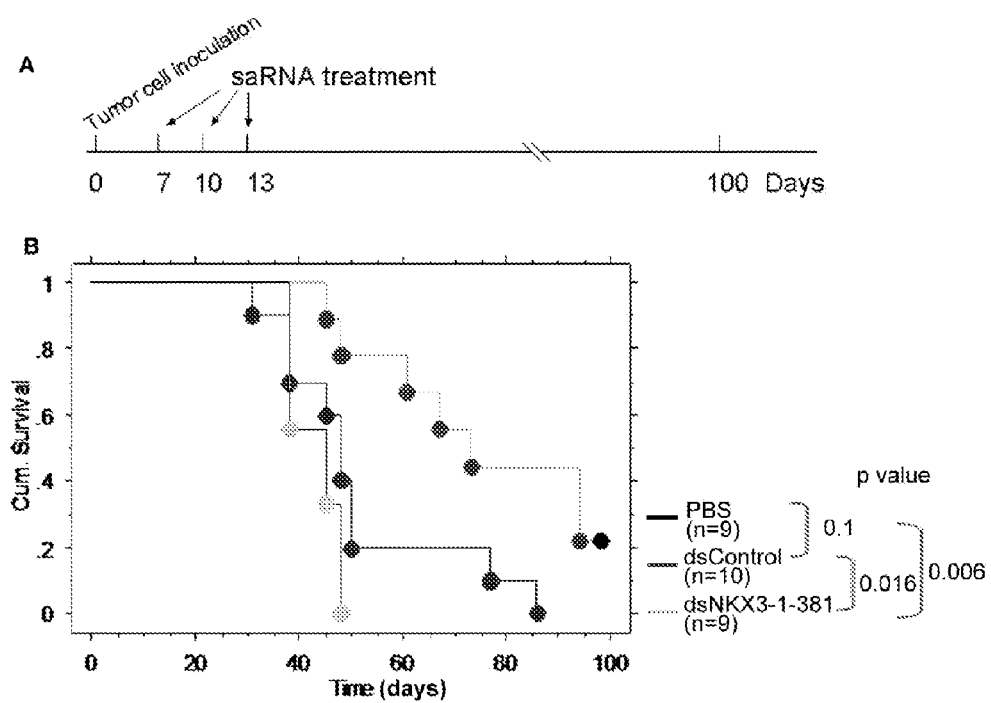
FIG. 10 shows that NKX3-1 saRNA treatment of xenograft prostate cancer extends mouse survival. Panel A, mice with established xenograft prostate cancer were treated with PBS, 150 μg NKX3-1 saRNA on day 7, 10 and 13. The treated mice were followed for 108 days. Panel B, survival was evaluated by Kaplan Meier analyses using the StatView statistical program. Study group mean survival days were calculated with the Kaplan Meier survival analysis. Survival days were compared by use of the Mantel-Cox test, and statistical significance was reached when $p<0.05$.

The average life span for PBS, dsControl and dsNKX3-1-381 group was 42.9, 51.0 and 74.4 days respectively, with a 73.4% (p=0.006) and 45.9% (p=0.016) increase in life span for dsNKX3-1-381 group compared to PBS and dsControl treatment respectively (FIG. 10). At day 108, two mice in the dsNKX3-1-381 group were free of tumors and considered as cured.

In summary, NKX3-1 saRNA exhibits potent activation of NKX3-1 in all prostate cancer cells tested and inhibits tumor cell proliferation in vitro. NKX3-1 saRNA also has potent antitumor activity in vivo and leads to eradication or significant shrinkage of established tumors.

Example 7

NKX3-1 Activation by saRNA Sensitizes Androgen-Independent Prostate Cancer Cell to Anti-Androgen Treatment Prostate cancer is the most commonly diagnosed male cancer after skin cancer and the second leading cause of cancer deaths in men in the United States. Early prostate cancer confined to the prostate is usually treated by radical prostatectomy and radiation. However, about one third of them will recur and become metastatic cancer. Once prostate cancer spreads out of the prostate, the disease is no loner curable. A common palliative treatment for advanced/metastatic prostate cancer is androgen ablation, to which most patients initially respond. However, eventually almost all cancers will fail this treatment and become androgen independent prostate cancer (AIPC). AIPC is a lethal form of cancer and there is no effective treatment for it.

Figure 11:
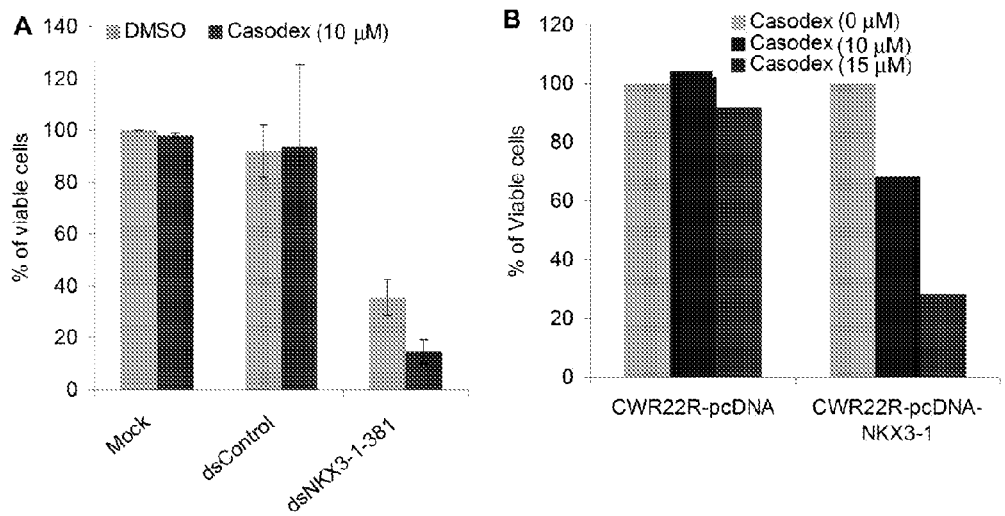
FIG. 11 shows that NKX3-1 overexpression sensitizes androgen independent cells to antiandrogen treatment. Panel A, CWR22R cells were transfected with the indicated dsRNA or mock transfected in the absence or presence of 10 μM Casodex. Viable cells were counted by trypan blue staining at 72 hrs following transfection. Results are means±SD of two independent experiments. Panel B, CWR22R cells stably expressing NKX3-1 (CWR22R-pcDNA-NKX3-1) or an empty vector (CWR22R-pcDNA) were treated with the indicated concentration of Casodex for 72 hrs. Viable cells were counted as in panel A.

To examine whether saRNA-mediated NKX3-1 activation could re-sensitize androgen independent prostate cancer cells to anti-androgen treatment, CWR22R cells were transfected saRNA for NKX3-1 activation CWR22R cells are AR positive and androgen-independent. The effect of saRNA for NKX3-1 activation was studied in the absence or presence of Casodex, an anti-androgen that binds to AR and inhibits its transcriptional activity. As shown in FIG. 11, panel A, dsNKX3-1-381 transfection alone caused 64.5% reduction in the number of viable cell compared to mock transfection. In the presence of 10 μM of Casodex, the inhibitory effect was further enhanced and reached 83.4% compared to mock transfection (FIG. 11, panel A). Casodex in combination with dsControl transfection did not significantly affect cell viability (FIG. 1, panel A). To validate this result, stable CWR22R cells that express either an empty vector (CWR22R-pcDNA) or NKX3-1 cDNA (CWR22R-pcDNA-NKX3-1) were treated with Casodex at three concentrations (0, 10 μM and 15 μM). At either concentration, Casodex caused no apparent cell death in CWR22R-pcDNA cells (FIG. 11, panel B), while in CWR22R-pcDNA-NKX3-1 cells, Casodex treatment resulted in a 32.7% and 72% reduction in the number of viable cells compared to vehicle control treated cells (FIG. 11, panel B). These findings reveal that NKX3-1 overexpression mediated by either saRNA or vectors can sensitize androgen independent prostate cancer cells to anti-androgen treatment.

Figure 12:
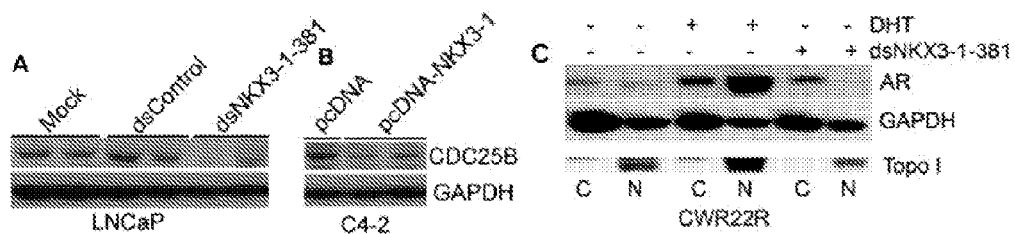
FIG. 12 shows that NKX3-1 suppressed CDC25B and inhibits AR translocation to the nucleus. Panel A, LNCaP cells were transfected with 50 nM of the indicated dsRNA or mock transfected for 72 hrs. Protein expression for CDC25B and GAPDH was analyzed by Western blotting. Panel B, C4-2 cells were transiently transfected with pcDNA empty vector or pcDNA-NKX3-1 for 72 hrs. CDC25B protein levels were detected by Western blotting. GAPDH served as a control for protein loading. Panel C, CWR22R cells were mock transfected (lane 1-4) or transfected with dsNKX3-1-381 (lane 5 and 6) for 72 hrs. At 48 hrs, mock transfected cells were treated with 10 nM DHT (lane 3 and 4). Proteins were isolated from both cytoplasmic and nuclear compartments and probed with antibody for AR. GAPDH served as a loading control for cytoplasmic proteins and Topo I for nuclear proteins.
Figure 13:
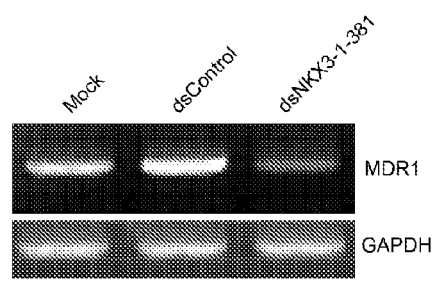
FIG. 13 illustrates that NKX3-1 saRNA inhibits MDR1 expression. CWR22R cells were transfected with 50 nM of the indicated dsRNA for 96 hrs. mRNA expression was analyzed by semi-quantitative RT-PCR.

To understand the mechanism of how NKX3-1 overexpression sensitizes prostate cancer cells to antiandrogen treatment, the expression of an AR coactivator CDC25B in LNCaP cells transfected with NKX3-1 saRNA and in C4-2 cells transiently transfected with NKX3-1 cDNA expressing vector was evaluated. As shown in FIG. 12, panels A and B, both NKX3-1 saRNA mediated and vector-based NKX3-1 overexpression significantly decreased CDC25B protein levels. AR distribution following NKX3-1 activation by NKX3-1 saRNA was next examined. AR nuclear translocation is greatly induced after treating CWR22R cells with dihydrotestosterone (DHT) (FIG. 12, panel C, lane 4). In contrast, dsNKX3-1-381 transfection in CWR22R caused complete disappearance of nuclear AR (FIG. 12, panel C, lane 6) despite there was a slight increase in cytoplasmic AR level (FIG. 12, panel C, lane 5) compared to untreated cells (FIG. 12, panel C, lane 1), suggesting that NKX3-1 activation could prevent AR from translocating to the nucleus to exert its transcriptional activity.

Taken together, these results reveal that NKX3-1 saRNA sensitizes androgen-independent prostate cancer cells to an anti-androgen agent through at least two potential mechanisms: suppressing AR translocation and inhibiting AR coactivators.

Example 8

NKX3-1 saRNA Inhibits MDR1 Expression

Multidrug resistance 1 (MDR1) encodes for P-glycoprotein, a 170-kDa, 12-segment, transmembrane calcium-dependent efflux pump that is responsible for decreased drug accumulation in multidrug-resistant cells and often mediates the development of resistance to anticancer drugs. Prostate cancer that is initially responsive may develop MDR during chemotherapy by overexpression of P-glycoprotein. NKX3-1 activation by NKX3-1 saRNA suppresses the expression of MDR1 gene (FIG. 3), which could lead to sensitization of prostate cancer cells to chemotherapy as have been demonstrated by RNAi mediated knockdown of MDR1 gene in prostate cancer cells.

Figure 14:
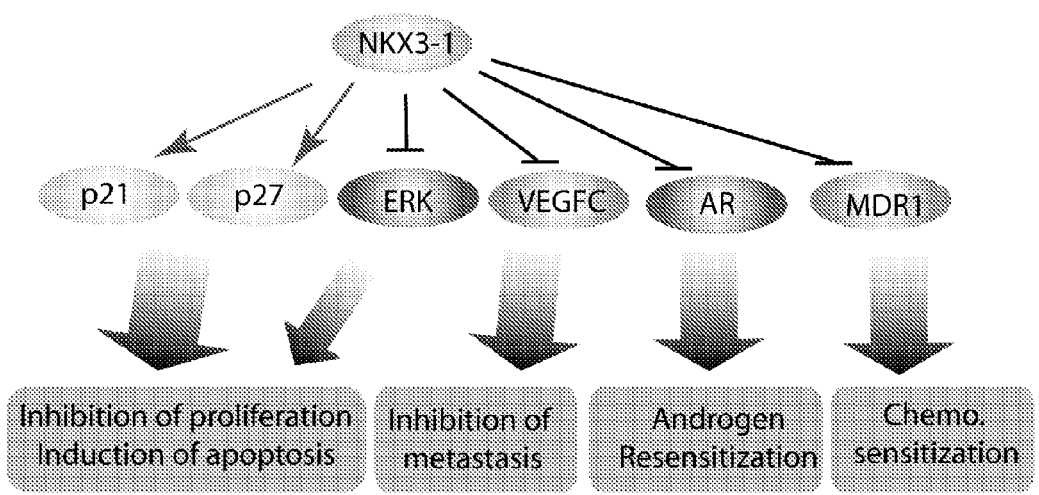
FIG. 14 is a model of NKX3-1 activation for the treatment of prostate cancer. NKX3-1 activation upregulates the expression of p21 and p27 and inhibits both ERK expression and phosphorylation, leading to cell proliferation inhibition and apoptosis. NKX3-1 activation may also inhibit tumor cell metastasis by suppressing the expression of VEGF-C. NKX3-1 activation sensitizes androgen-independent prostate cancer cells to anti-androgen treatment and potentiates prostate cancer cells to chemotherapy by suppression the AR and MDR1 pathways, respectively.

In summary, through in vitro and in vivo studies, NKX3-1 is identified herein as a druggable saRNA target. NKX3-1 can be activated by one of the potent saRNA dsNKX3-1-381 in all prostate cancer cell lines examined. RNAa-mediated activation of NKX3-1 leads to proliferative inhibition and apoptosis of prostate cancer cells, sensitization of androgen-independent prostate cancer cells to antiandrogen treatment. Intratumoral delivery of NKX3-1 saRNA dramatically inhibited tumor growth and prolonged animal survival in xenograft prostate cancer models. These effects are mediated through multiple signaling pathways including the upregulation of the cell cycle negative regulators p21 and p27, the suppression of ERK expression and phosphorylation, and downregulation of VEGFC and MDR1, and most importantly the suppression of AR transcriptional activity (FIG. 14).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

References (The Following References Pertain to Examples 1-8 Above)

1. Li L C, Okino S T, Zhao H, et al. Small dsRNAs induce transcriptional activation in human cells. Proceedings of the National Academy of Sciences of the United States of America 2006 Nov. 14; 103(46):17337-42.
2. Li L C. The multifaceted small RNAs. RNA Biol 2008 April-June; 5(2):61-4.
3. Janowski B A, Younger S T, Hardy D B, Ram R, Huffman K E, Corey D R. Activating gene expression in mammalian cells with promoter-targeted duplex RNAs. Nature chemical biology 2007 March; 3(3):166-73.
4. Huang V, Qin Y, Wang J, et al. RNAa Is Conserved in Mammalian Cells. PLoS One 2010; 5(1):e8848.
5. Place R F, Li L C, Pookot D, Noonan E J, Dahiya R. MicroRNA-373 induces expression of genes with complementary promoter sequences. Proceedings of the National Academy of Sciences of the United States of America 2008 Feb. 5; 105(5):1608-13.
6. Chen Z, Place R F, Jia Z J, Pookot D, Dahiya R, Li L C. Antitumor effect of dsRNA-induced p21(WAF1/CIP1) gene activation in human bladder cancer cells. Mol Cancer Ther 2008 March; 7(3):698-703.
7. Mao Q, Li Y, Zheng X, et al. Up-regulation of E-cadherin by small activating RNA inhibits cell invasion and migration in 5637 human bladder cancer cells. Biochem Biophys Res Commun 2008 Oct. 31; 375(4):566-70.
8. Yang K, Zheng X Y, Qin J, et al. Up-regulation of p21WAF1/Cip1 by saRNA induces G1-phase arrest and apoptosis in T24 human bladder cancer cells. Cancer letters 2008 Jul. 8; 265(2):206-14.
9. Aigner A. Gene silencing through RNA interference (RNAi) in vivo: strategies based on the direct application of siRNAs. J Biotechnol 2006 Jun. 25; 124(1):12-25.
10. Kim M J, Bhatia-Gaur R, Banach-Petrosky W A, et al. Nkx3.1 mutant mice recapitulate early stages of prostate carcinogenesis. Cancer Res 2002 Jun. 1; 62(11):2999-3004.
11. Bieberich C J, Fujita K, He W W, Jay G. Prostate-specific and androgen-dependent expression of a novel homeobox gene. J Biol Chem 1996 Dec. 13; 271(50):31779-82.
12. He W W, Sciavolino P J, Wing J, et al. A novel human prostate-specific, androgen-regulated homeobox gene (NKX3.1) that maps to 8p21, a region frequently deleted in prostate cancer. Genomics 1997 Jul. 1; 43(1):69-77.
13. Lundgren R, Mandahl N, Heim S, Limon J, Henrikson H, Mitelman F. Cytogenetic analysis of 57 primary prostatic adenocarcinomas. Genes Chromosomes Cancer 1992 January; 4(1):16-24.
14. MacGrogan D, Levy A, Bostwick D, Wagner M, Wells D, Bookstein R. Loss of chromosome arm 8p loci in prostate cancer: mapping by quantitative allelic imbalance. Genes Chromosomes Cancer 1994 July; 10(3):151-9.
15. Ishkanian A S, Mallof C A, Ho J, et al. High-resolution array CGH identifies novel regions of genomic alteration in intermediate-risk prostate cancer. Prostate 2009 Jul. 1; 69(10):1091-100.
16. Asatiani E, Huang W X, Wang A, et al. Deletion, methylation, and expression of the NKX3.1 suppressor gene in primary human prostate cancer. Cancer Res 2005 Feb. 15; 65(4):1164-73.
17. Bhatia-Gaur R, Donjacour A A, Sciavolino P J, et al. Roles for Nkx3.1 in prostate development and cancer. Genes Dev 1999 Apr. 15; 13(8):966-77.
18. Tanaka M, Komuro I, Inagaki H, Jenkins N A, Copeland N G, Izumo S, Nkx3.1, a murine homolog of Ddrosophila bagpipe, regulates epithelial ductal branching and proliferation of the prostate and palatine glands. Dev Dyn 2000 October; 219(2):248-60.
19. Schneider A, Brand T, Zweigerdt R, Arnold H. Targeted disruption of the Nkx3.1 gene in mice results in morphogenetic defects of minor salivary glands: parallels to glandular duct morphogenesis in prostate. Mech Dev 2000 July; 95(1-2):163-74.
20. Abdulkadir S A, Magee J A, Peters T J, et al. Conditional loss of Nkx3.1 in adult mice induces prostatic intraepithelial neoplasia. Mol Cell Biol 2002 March; 22(5):1495-503.
21. Bethel C R, Faith D, Li X, et al. Decreased NKX3.1 protein expression in focal prostatic atrophy, prostatic intraepithelial neoplasia, and adenocarcinoma: association with gleason score and chromosome 8p deletion. Cancer Res 2006 Nov. 15; 66(22):10683-90.
22. Bowen C, Bubendorf L, Voeller H J, et al. Loss of NKX3.1 expression in human prostate cancers correlates with tumor progression. Cancer Res 2000 Nov. 1; 60(21):6111-5.
23. Voeller H J, Augustus M, Madike V, Bova G S, Carter K C, Gelmann E P. Coding region of NKX3.1, a prostate-spe- 23. cific homeobox gene on 8p21, is not mutated in human prostate cancers. Cancer Res 1997 Oct. 15; 57(20):4455-9.
24. Lind G E, Skotheim R I, Fraga M F, et al. The loss of NKX3.1 expression in testicular—and prostate—cancers is not caused by promoter hypermethylation. Mol Cancer 2005 Feb. 3; 4(1):8.
25. Korkmaz K S, Korkmaz C G, Ragnhildstveit E, Kizildag S, Pretlow T G, Saatcioglu F. Full-length cDNA sequence and genomic organization of human NKX3A-alternative forms and regulation by both androgens and estrogens. Gene 2000 Dec. 30; 260(1-2):25-36.
26. Harvey R P. NK-2 homeobox genes and heart development. Dev Biol 1996 Sep. 15; 178(2):203-16.
27. Lei Q, Jiao J, Xin L, et al. NKX3.1 stabilizes p53, inhibits AKT activation, and blocks prostate cancer initiation caused by PTEN loss. Cancer Cell 2006 May; 9(5):367-78.
28. Steadman D J, Giuffrida D, Gelmann E P. DNA-binding sequence of the human prostate-specific homeodomain protein NKX3.1. Nucleic Acids Res 2000 Jun. 15; 28(12): 2389-95.
29. Abate-Shen C, Shen M M, Gelmann E. Integrating differentiation and cancer: the Nkx3.1 homeobox gene in prostate organogenesis and carcinogenesis. Differentiation 2008 July; 76(6):717-27.
30. Zhang P, Liu W, Zhang J, et al. Gene expression profiles in the PC-3 human prostate cancer cells induced by NKX3.1. Mol Biol Rep 2009 May 22.
31. Zhang H, Muders M H, Li J, Rinaldo F, Tindall D J, Datta K. Loss of NKX3.1 favors vascular endothelial growth factor-C expression in prostate cancer. Cancer Res 2008 Nov. 1; 68(21):8770-8.
32. Karpanen T, Egeblad M, Karkkainen M J, et al. Vascular endothelial growth factor C promotes tumor lymphangiogenesis and intralymphatic tumor growth. Cancer Res 2001 Mar. 1; 61(5):1786-90.
33. Skobe M, Hawighorst T, Jackson D G, et al. Induction of tumor lymphangiogenesis by VEGF-C promotes breast cancer metastasis. Nat Med 2001 February; 7(2):192-8.
34. Thomson A A, Cunha G R. Prostatic growth and development are regulated by FGF10. Development 1999 August; 126(16):3693-701.
35. Thomson A A. Role of androgens and fibroblast growth factors in prostatic development. Reproduction 2001 February; 121(2):187-95.
36. Kuslak S L, Marker P C. Fibroblast growth factor receptor signaling through MEK-ERK is required for prostate bud induction. Differentiation 2007 September; 75(7):638-51.
37. Misra U K, Pizzo S V. Epac1-induced cellular proliferation in prostate cancer cells is mediated by B-Raf/ERK and mTOR signaling cascades. J Cell Biochem 2009 Nov. 1; 108(4):998-1011.
38. Wegiel B, Jiborn T, Abrahamson M, et al. Cystatin C is downregulated in prostate cancer and modulates invasion of prostate cancer cells via MAPK/Erk and androgen receptor pathways. PLoS One 2009; 4(11):e7953.
39. Oh H Y, Lee E J, Yoon S, Chung B H, Cho K S, Hong S J. Cholesterol level of lipid raft microdomains regulates apoptotic cell death in prostate cancer cells through EGFR-mediated Akt and ERK signal transduction. Prostate 2007 Jul. 1; 67(10):1061-9.
40. Kinkade C W, Castillo-Martin M, Puzio-Kuter A, et al. Targeting AKT/mTOR and ERK MAPK signaling inhibits hormone-refractory prostate cancer in a preclinical mouse model. J Clin Invest 2008 September; 118(9):3051-64.

The following methods and materials were used in the examples 9-13.

Materials and Methods dsRNA Design and Synthesis

One kilobase (kb) of the human KLF4 promoter was scanned for dsRNA target sites based on rational design rules as previously reported (1). BLAST searches were performed against the NCBI genome database to confirm that each target site did not share significant homology with other known sequences in the human genome. All dsRNAs were synthesized by Invitrogen (Carlsbad, Calif.) with dTdT 3'-overhangs. A control dsRNA (dsControl) was also designed that lacked significant homology to all known human sequences. All dsRNA sequences are listed in Table 2 below.

TABLE 2

Sequences for dsRNAs and oligonucleotide primers

| dsRNA name* | Sequence (5' - 3') |
|---|---|
| dsKLF4-496 | Sense: GAA CCC AGG GAG CCG ACA A[dT][dT] (SEQ ID NO: 5) |
| | Antisense: UUG UCG GCU CCC UGG GUU C[dT][dT] (SEQ ID NO: 6) |
| dsKLF4-525 | Sense: CGC UGA CCC CAC CAG UCU U[dT][dT] (SEQ ID NO: 7) |
| | Antisense: AAG ACU GGU GGG GUC AGC G[dT][dT] (SEQ ID NO: 8) |
| dsKLF4-168 | Sense: GCU GUA GCG AAG GAA GUU A[dT][dT] (SEQ ID NO: 9) |
| | Antisense: UAA CUU CCU UCG CUA CAG C[dT][dT] (SEQ ID NO: 10) |
| dsKLF4-261 | Sense: GAU UUA GCU GCC AUA GCA A[dT][dT] (SEQ ID NO: 11) |
| | Antisense: UUG CUA UGG CAG CUA AAU C[dT][dT] (SEQ ID NO: 12) |
| dsControl | Sense: ACU ACU GAG UGA CAG UAG A[dT][dT] (SEQ ID NO: 13) |
| | Antisense: UCU ACU GUC ACU CAG UAG U[dT][dT] (SEQ ID NO: 14) |

*Number in dsRNA name denotes target location relative to the transcription start site.

| RT-PCR primers | |
|---|---|
| Primer name | Sequence (5' - 3') |
| KLF4 | Sense: ACCCACACTTGTGATTACGC (SEQ ID NO: 15) |
| | Antisense: CCGTGTGTTTACGGTAGTGC (SEQ ID NO: 16) |
| CENPE | Sense: TGCAAGGAACGGAATTTACA (SEQ ID NO: 17) |
| | Antisense: ACCTGGCTGAGAATCCACAC (SEQ ID NO: 18) |
| BUB1 | Sense: TTATCTGCTGGCTTGGCACT (SEQ ID NO: 19) |
| | Antisense: GCAGCAACCCCAAAGTAATC (SEQ ID NO: 20) |
| MAD2L1 | Sense: GATGACAGTGCACCCAGAGA (SEQ ID NO: 21) |
| | Antisense: CCGACTCTTCCCATTTTTCA (SEQ ID NO: 22) |

TABLE 2-continued

| | |
|---|---|
| p57 | Sense: CAGAACCGCTGGGATTACGACTT (SEQ ID NO: 23) |
| | Antisense: AGTCGCTGTCCACTTCGGTCCACT (SEQ ID NO: 24) |
| GAPDH | Sense: TGGGTGTGAACCATGAGAAG (SEQ ID NO: 25) |
| | Antisense: GTGTCGCTGTTGAAGTCAGA (SEQ ID NO: 26) |
| ACTB (for qPCR) | Sense: GCAAAGACCTGTACGCCAAC (SEQ ID NO: 27) |
| | Antisense: GTACTTGCGCTCAGGAGGAG (SEQ ID NO: 28) |

Bisulfite genomic sequencing PCR primers

Primer name Sequence (5' - 3')

| | |
|---|---|
| KLF4-BSP | Sense: GGAGATGGAGGGTTGGATGAGTT (SEQ ID NO: 29) |
| | Antisense: TAACRCCAACCAAACAACTAAC† (SEQ ID NO: 30) |
| | †R: Degenerate nucleotide corresponding to G and A |

Cell Culture and Transfection

PC-3, DU-145, DuPro, LNCaP, and BPH1 cells were maintained in RPMI-1640 medium supplemented with 10% fetal bovine serum (FBS), 2 mM L-glutamine, penicillin (100 U/ml), and streptomycin (100 µg/ml) in a humidified atmosphere of 5% $CO_2$ maintained at 37° C. RWPE-1 and PWR-1E cells were cultured in keratinocyte-serum-free medium supplemented with 5 ng/ml human recombinant epidermal growth factor, and 0.05 mg/ml bovine pituitary extract. Transfection of dsRNA was carried out by using Lipofectamine RNAiMax (Invitrogen) according to the manufacturer's protocol for reverse transfection.

Analysis and Quantification of mRNA Expression

Total RNA was isolated by using the RNeasy Mini Kit (Qiagen, Valencia, Calif.). M-MLV reverse transcriptase (Promega, Madison, Wis.) and oligo(dT) primers were utilized to reverse transcribe 1 µg of RNA. The resulting cDNA samples were amplified by PCR using primers specific for KLF4 or GAPDH and visualized on an agarose gel. To quantify gene expression, real-time PCR was performed using gene-specific primer sets in conjunction with the Power SYBR Green PCR Master Mix (Applied Biosystems, Foster City, Calif.). Real-time expression data was normalized to β-actin levels. All primer sequences are listed in Table 2 above.

Immunoblot Analysis

Cells were washed with PBS and lysed in RIPA buffer (50 mM Tris, pH 7.4, 150 mM NaCl, 1% Triton X-100, 0.5% deoxycholate, 0.1% SDS) containing protease inhibitor cocktail for 15 min at 4° C. Cell lysates were centrifuged and supernatants were collected. Equivalent amounts of proteins were resolved on SDS-PAGE gels and transferred to PVDF membranes. The resulting blots were blocked in 5% nonfat dry milk overnight at 4° C. The following day blots were incubated with primary antibodies to detect specific proteins. Appropriate HRP-conjugated secondary antibodies and supersignal west pico chemiluminescent substrate (Thermo Fisher Scientific, Waltham, Mass.) were used to visualize antigen-antibody complexes. Primary antibodies included gKLF4 (H-180) (1:2000 dilution; Santa Cruz Biotechnology, Santa Cruz, Calif.), p21$^{Waf1/Cip}$1 (12D1), p27$^{Kip1}$, p57$^{Kip2}$, CCNB1 (V152) (1:1000 dilution; Cell Signaling Technology, Beverly, Mass.), and β-actin (AC-15) (1:3000 dilution; Sigma-Aldrich, St. Louis, Mo.).

Comparative Metaprofiling of cDNA Expression Data

The Oncomine Premium version (15) was accessed to perform differential expression analysis of KLF4 in existing prostate cancer microarray datasets by setting a threshold value for gene rank at 10% and for p-value at 0.05.

Cell Viability Assay

Cells were transfected with dsRNA for ~12 hours. Following treatments, cells were transferred to 96-well microplates and seeded at a density of ~800 cells per well. Cell viability was subsequently determined every 24 hours for 6 days by using MTS reagent CellTiter 96 AQueous One Solution (Promega) according to the manufacture's protocol. Absorbance was measured on a 96-well plate reader at 490 nm.

Colony Formation Assay

Exponentially growing cells were plated at ~1000 cells per well in 6-well plates and transfected with using Lipofectamine RNAiMax (Invitrogen) by following the reverse transfection protocol. Culture medium was changed every 3 days. Colony formation was analyzed 12 days following transfection by staining cells with 0.05% crystal violet solution for 1 hr.

Cell Cycle Analysis

Transfected cells were trypsinized and centrifuged at 2000×g for 5 mM at 4° C. in complete medium. Cell pellets ($1 \times 10^6$ cells) were resuspended in 1 ml of cold saline GM solution (6.1 mM glucose, 1.5 mM NaCl, 5.4 mM KCl, 1.5 mM $Na_2HPO_4$, 0.9 mM $KH_2PO_4$, 0.5 mM EDTA) and fixed in 3 ml of 100% ethanol overnight at 4° C. Cells were then washed once at 2000×g for 5 min in PBS with 5 mM EDTA and resuspended in 1 ml of propidium iodide (PI) staining solution (30 µg/ml PI, 300 µg/ml RNAse A in PBS). Cells were stained for 1 hour at room temperature in the dark and subsequently filtered through 30 µm nylon mesh. Analysis was performed on a FACSCaliber flow cytometer (Becton Dickinson, Franklin Lakes, N.J.). A total of 10,000 events were collected and PI intensity was analyzed using the FL2 channel for relative DNA content. Forward and side scatter gates and a doublet discrimination plot were set to include whole and individual cell populations, respectively. The resulting data was analyzed using the FlowJo software (Tree Star, Inc., Ashland, Oreg.) to determine cell cycle distribution and apoptotic (sub-diploid) cell fraction.

Bisulfite Genomic Sequencing

Genomic DNA was isolated from cultured cells using the QIAamp DNA mini kit (Qiagen). Bisulfite modification of DNA was performed by using the EZ DNA Methylation-Direct kit (Zymo Research, Orange, Calif.) according to the manufacturer's protocol. Primers capable of amplifying bisulfite-modified DNA within the KLF4 promoter (Supplementary Table S1) were designed by using the online program MethPrimer developed in our laboratory (56). Resulting DNA was subject to sequencing analysis to determine the methylation status within the amplified sequence.

Retrovirus-Based Overexpression of KLF4

A retroviral human KLF4 cDNA expression vector (pMXs-hKLF4) previously utilized in KLF4 overxpression studies (57) was obtained from Addgene (Cambridge, Mass.). An empty vector (pMXs-EV) was generated by removing the KLF4 gene from the retroviral sequence. Retrovirus particles were generated by transfecting 293FT cells (Invitrogen) with retroviral vectors for 48 hours. Media was harvested and used to infect PC-3 and DuPro cells. Cells were harvested for gene expression analysis, clonogenicity and proliferation assays.

Example 9

KLF4 is Down-Regulated in Prostate Cancer Cell Lines and Tissue

Figure 15:
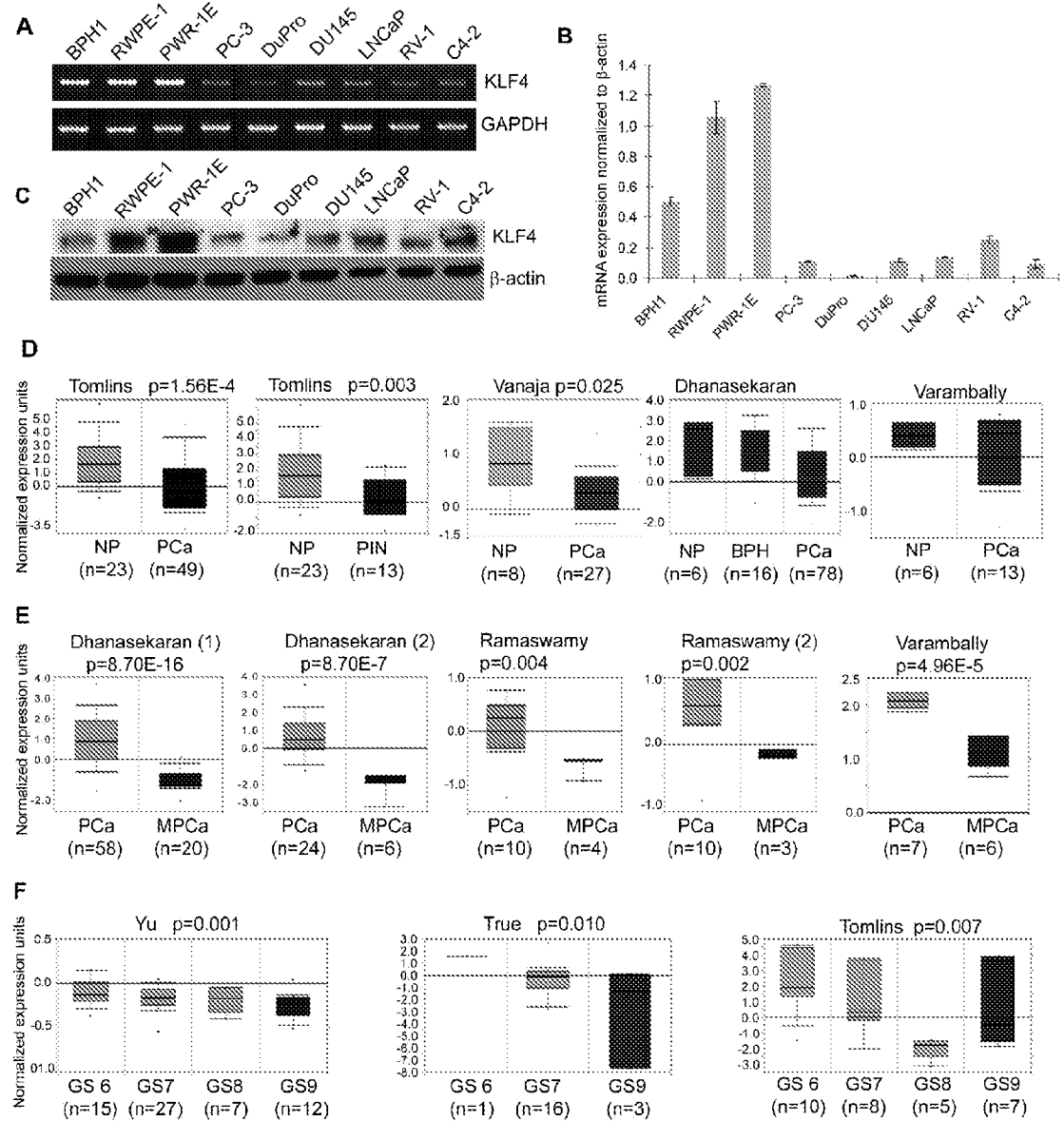
FIG. 15 illustrates that KLF4 expression is downregulated in prostate cancer cell lines and tissues. Panel A, KLF4 mRNA expression levels were evaluated by semiquantitative RT-PCR in non-tumorigenic prostate epithelial (RWPE-1 and PWR-1E), benign prostate hyperplasia (BPH1), and prostate cancer (PC-3, DuPro, DU-145, LNCaP, RV-1, and C4-2) cell lines. GAPDH was also amplified and served as an endogenous control. Panel B, Relative expression of KLF4 was determined by real-time PCR (mean±SEM from two independent experiments). Expression values of KLF4 were normalized to β-actin levels. Panel C, KLF4 and β-actin protein levels were detected by immunoblot analysis. β-actin served as a loading control. KLF4 expression was mined using the Oncomine database. Panel D, In three datasets, KLF4 mRNA expression was significantly downregulated in PIN and primary prostate cancer compared to normal prostate. Panel E, Significant downregulation of KLF4 is also significant in 5 datasets comparing metastatic prostate cancer to primary prostate cancer. Panel F, Decreased KLF4 expression with increased Gleason scores was found in 3 datasets.

KLF4 is a known tumor suppressor gene in gastrointestinal tract cancer (11-14). KLF4 expression levels in a panel of 9 prostate cell lines including 6 cancerous (PC-3, DuPro, DU145, LNCaP, RV-1, and C4-2) and 3 non-tumorigenic/benign (RWPE-1, PWR-1E, and BPH1) cell lines were evaluated. Analysis of mRNA expression by RT-PCR revealed that KLF4 transcript levels are lower in all cancerous cell lines compared to the non-tumorigenic/benign controls (FIG. 15, panel A). Real-time PCR confirmed that KLF4 mRNA expression was significantly down-regulated by ≥80% in each prostate cancer cell line compared to levels in RWPE-1 and PWR-1E cells (FIG. 15, panel B) Immunoblot analysis indicated that KLF4 protein levels correlated to that of mRNA in all cell lines (FIG. 15, panel C). To ask whether KLF4 expression is also downregulated in prostate cancer samples, the Oncomine database, an online application that provides tools for profiling gene expression on a large collection of microarray datasets (15) was mined. In three datasets, KLF4 mRNA expression was significantly downregulated in PIN and primary prostate cancer compared to normal prostate (16-19) (FIG. 15, panel D). Significant downregulation of KLF4 is also significant in 5 datasets comparing metastatic prostate cancer to primary prostate cancer (17, 19-22) (FIG. 15, panel E). Decreased KLF4 expression with increased Gleason scores was found in 3 datasets (16, 23, 24) (FIG. 15, panel F). Taken together, the prevalent downregulation of KLF4 in prostate cancer cells indicates that KLF4 may possess a tumor suppressor role.

The human KLF4 promoter contains a CpG island approximately 1 kb long that extends into the first exon. Previous studies have found that DNA hypermethylation of this region is associated with KLF4 inactivation in a subset of gastric and colon cancer cell lines and tissues (11, 12). Therefore, the methylation status in a proximal region of the KLF4 promoter was evaluated by bisulfite genomic sequencing in prostate cancer cell lines (PC-3, DuPro, DU145 and LNCaP). Interestingly, DNA methylation was only detected in LNCaP. This data suggests that methylation of this region does not play a significant role in KLF4 downregulation in prostate cancer cell lines.

Example 10

Promoter-Targeting saRNAs Induced KLF4 Expression in Prostate Cancer Cells

Figure 16:
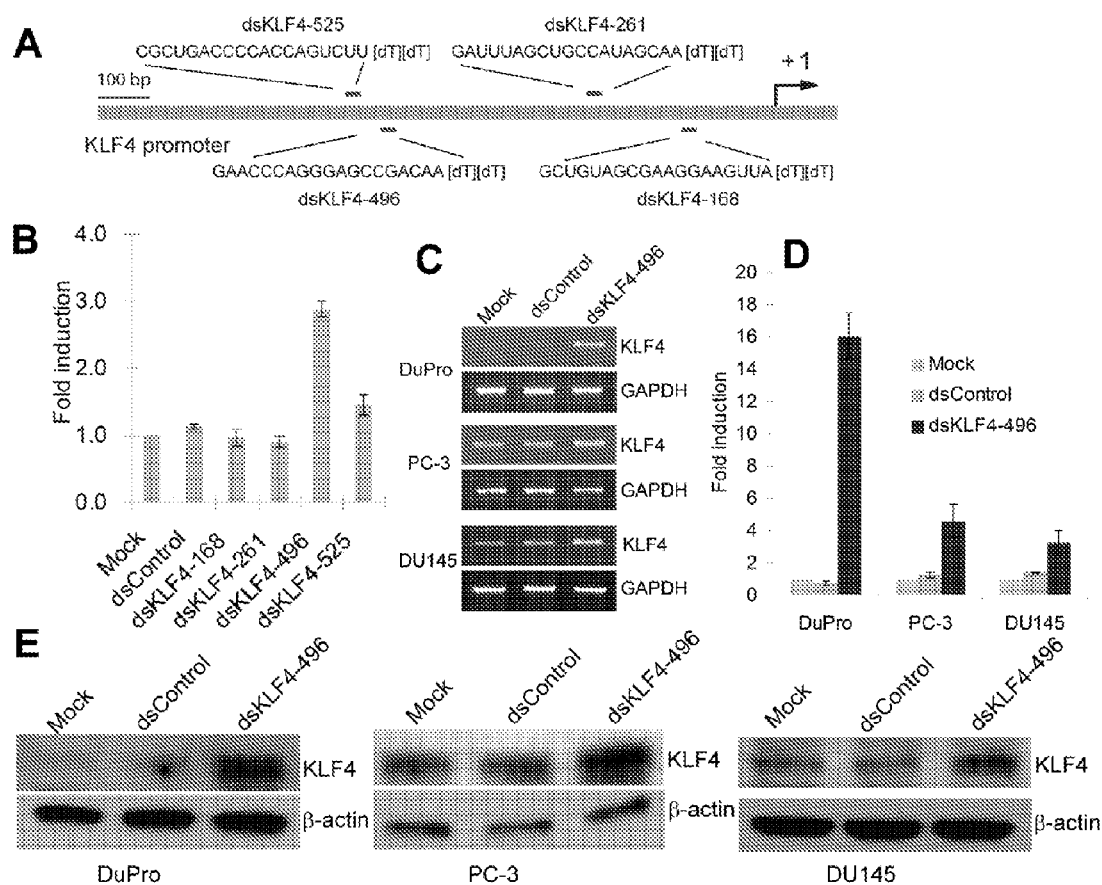
FIG. 16 depicts increased KLF4 expression by KLF4 saRNA in prostate cancer cell lines. Panel A. A schematic representation of the KLF4 promoter. Indicated are the locations of each dsRNA target site relative to the transcription start site (+1) and the sense sequence of the corresponding dsRNA (dsKLF4-525 (SEQ ID NO: 7); dsKLF4-261 (SEQ ID NO: 11); dsKLF4-496 (SEQ ID NO: 5); and dsKLF4-168 (SEQ ID NO: fl. Panel B. PC-3 cells were transfected with 50 nM concentrations of the indicated dsRNAs for 72 hours. Mock samples were transfected in the absence of dsRNA. KLF4 expression was assessed by real-time PCR. Results are plotted as fold change relative to mock transfections (mean±SEM of two independent experiments). Panel C. DuPro, PC-3, and DU145 cells were transfected with 50 nM dsControl or dsKLF-496 for 96 hours. KLF4 and GAPDH expression levels were assessed by semiquantitative RT-PCR. Panel D. Cells were transfected as in C. Relative KLF4 expression was quantified by real-time PCR in each cell line (mean±SEM from three independent experiments). KLF4 expression was normalized to β-actin levels. Panel E. Cells were transfected as in panel C. KLF4 and β-actin protein levels were detected by immunoblot analysis using protein-specific antibodies. β-actin served as a loading control.

To test whether KLF4 has a tumor suppressor role in prostate cancer cells, KLF4 expression was activated by RNAa (also referred to as saran or dsRNA) and then evaluate the functional consequence of KLF4 restoration on prostate cancer cells. 4 candidate dsRNAs (dsKLF4-525, dsKLF4-496, dsKLF4-261, and dsKLF4-168) were designed targeting the KLF4 promoter at sites ranging from −525 to −168 relative to the transcription start site (FIG. 16, panel A) according to rules derived from our previous study (1). BLAST searches were performed to confirm that each target site did not share significant homology with other sequences in the human genome. A non-specific dsRNA (dsControl) was designed to serve as a control. To screen for RNAa activity, these dsRNAs were transfected into PC-3 cells and evaluated KLF4 expression by real-time PCR 3 days following transfection. Compared to controls, dsKLF4-496 and dsKLF4-525 induced KLF4 expression by ~3.0- and 1.5-fold, respectively, while dsKLF4-168 and dsKLF4-261 did not significantly alter KLF4 levels (FIG. 16, panel B). Time-course experiments further indicated that optimal levels of KLF4 induction (~4.2-fold) were achieved by day 4 in PC-3 cells.

To determine if KLF4 was susceptible to RNAa in other prostate cancer cells lines, DuPro, PC-3, DU-145, and LNCaP cells were transfected with dsKLF4-496 which possessed the most potent RNAa activity in PC-3 cells. Four days following transfection, dsKLF4-496 induced KLF4 mRNA expression by 16, 4.6 and 3.3-fold in DuPro, PC-3, and DU145 cells respectively (FIG. 16, panels C and D). LNCaP cells were insensitive to dsKLF4-496 as it failed to activate KLF4 expression (Data not shown). Consistent with mRNA induction, KLF4 protein levels as assessed by Western blotting assays were also induced by dsKLF4-496 in each of the sensitive cell lines (FIG. 16, panel E).

Figure 17:
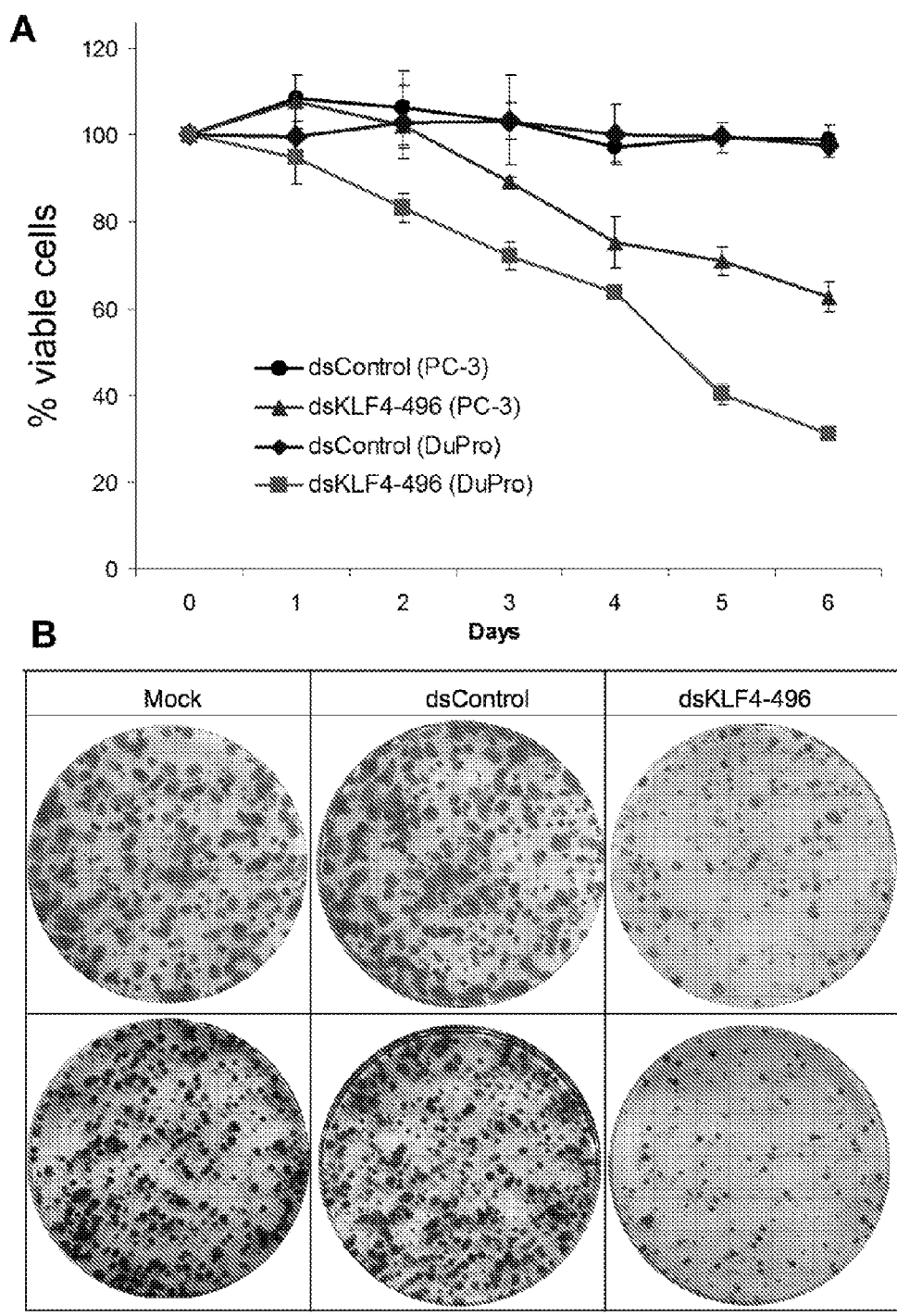
FIG. 17 shows that increased expression of KLF4 by saRNA inhibits prostate cancer cell viability and clonogenicity. Panel A. PC-3 and DuPro cells were transfected with 50 nM dsRNA for the indicated lengths of time. MTS reagent was utilized to quantify cell viability at each time point. Data is plotted as the mean±SEM of two independent experiments relative to mock treatments. Panel B. PC-3 and DuPro cells were plated at 1000 cells in 6-well tissue culture plates and transfected with mock, dsControl, or dsKLF4-496. Cells were grown for 12 days and analyzed for colony formation by staining with crystal violet. Shown are representative photographs taken of tissue culture plates from each dsRNA treatment group following staining for colony formation.

Example 11 saRNA-Mediated KLF4 Overexpression Inhibited Growth and Survival of Prostate Cancer Cells In accordance with a tumor suppressor role found in other types of cancer (11, 14, 25, 26), KLF4 overexpression mediated by saRNA in prostate cancer cells resulted in inhibited growth and survival. Prostate cancer cells transfected with either dsKLF4-496 (also referred to as saKLF4-496) or dsKLF4-525 (also referred to as saKLF4-525) displayed altered morphology and decreased cell density characteristic of impeded growth. Quantitative analysis by MTS assay indicated that PC-3 and DuPro cell viability steadily decreased following dsKLF4-496 transfection (FIG. 17, panel A). By day 6, growth was inhibited by ~40% and ~70% in PC-3 and DuPro cells, respectively. Clonogenicity assays also revealed that KLF4 overexpression reduced the number and size of colonies formed by PC-3 and DuPro cells (FIG. 17, panel B).

Example 12

Figure 18:
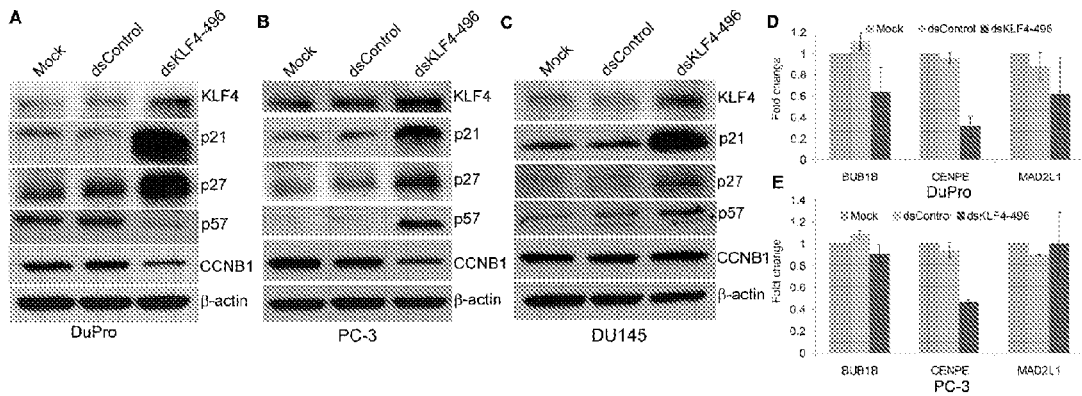
FIG. 18 shows that KLF4 activation alters the expression of cell cycle-related genes in prostate cancer cells. Panels A-C. DuPro, PC-3, and DU145 cells were transfected with 50 nM dsControl or dsKLF-496 for 96 hours. Mock samples were transfected in the absence of dsRNA. Total protein was extracted and levels of KLF4, p21, CCNB1, p27, p57, and β-actin were determined by immunoblot analysis. β-actin served as a loading control. Panels D and E. DuPro (Panel D) and PC-3 (Panel E) cells were transfected with the indicated dsRNAs for 96 hours. Relative expression levels of BUB1B, CENPE, and MAD2L1 were quantified by real-time PCR (mean±SEM from three independent experiments). Expression values were normalized to β-actin levels.

RNAa-Mediated KLF4 Overexpression Modulated Cell Cycle Related Genes and Arrested the Cell Cycle To understand the mechanism underlying the antigrowth effect of RNAa-mediated KLF4 activation in prostate cancer cells, the expression of several cell cycle related genes known to be regulated by KLF4 including cyclin-dependent kinase inhibitors $p21^{WAF1/CIP1}$ (p21), $p27^{KIP1}$ (p27) and $p57^{KIP2}$ (p57) and Cyclin B1 (CCNB1) was assessed (14, 27-30). As shown in FIG. 18, panels A-C, dsKLF4-496 induced KLF4 levels and altered the expression of several downstream targets in DuPro, PC-3 and DU145 cells. Of interest, p21 and p27 expression was upregulated in all three cell lines, while CCNB1 was only selectively downregulated in DuPro and PC-3 cells (FIG. 18, panels A-C). Levels of p57 protein also increased in PC-3 and DU145 cells, but markedly decreased in DuPro cells (FIG. 18, panels A-C). In order to determine if protein levels correlated to p57 transcription, we utilized real-time PCR to quantify p57 mRNA levels. p57 mRNA expression increased in all three cell lines suggesting p57 is differentially regulated by post-transcriptional mechanisms in DuPro cells following KLF4 activation.

KLF4 has also been shown to downregulate genes involved in chromosome segregation and execution of the mitotic checkpoint including CENPE (centromere protein E), MAD2L1 (mitotic arrest deficient 2-like 1), and BUB1B (budding uninhibited by benzimidazoles 1 homolog B) (27). Mouse embryonic fibroblast null for KLF4 are genetically unstable as evidenced by the presence of aneuploidy, chromosome aberration and centrosome amplification, suggesting a role for KLF4 in maintaining genetic stability (31). Therefore, we also evaluated the expression of CENPE, BUB1B and MAD2L1 in DuPro and PC-3 cells following dsKLF4-496 transfection. In DuPro cells, BUB1B, CENPE, and MAD2L1 were down-regulated by dsKLF4-496, while only CENPE significantly declined in PC-3 cells (FIG. 18, panels D and E). This data indicates that the RNAa-based overexpression of KLF4 produced a functional protein capable of modulating the expression of known downstream genes that may have functional significance in regulating cell cycle progression in prostate cancer cells.

Figure 19:
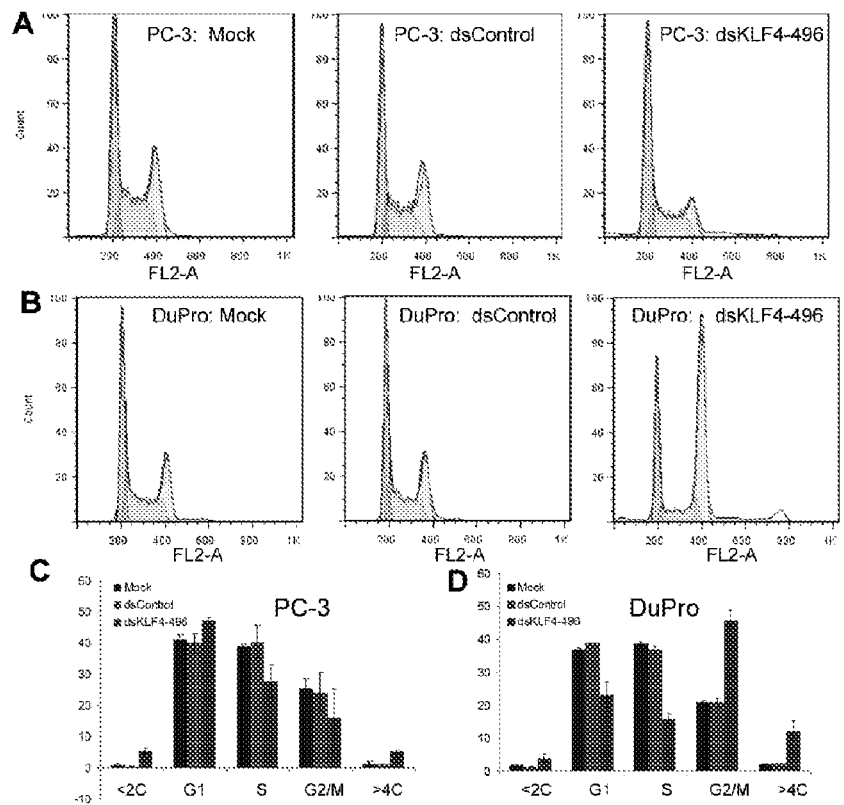
FIG. 19 illustrates that KLF4 inhibits cell cycle progression in prostate cancer cells. Panels A and B. PC-3 (Panel A) and DuPro (Panel B) cells were transfected with mock, dsControl, or dsKLF4-496 for 72 hours. Floating and attached cells were collected, stained with PI, and processed for analysis by flow cytometry to measure DNA content. Shown are representative FL2A histograms. Panels C and D. Flow cytometry data from PC-3 (C) and DuPro (D) cells was analyzed to determine cell cycle distribution. Percentages of sub-diploid/apoptotic (<2C) and polyploid (>4C) cells were calculated from entire gated whole-cell populations, while cell cycle distribution (G0/G1, S, and G2/M) was determined from only surviving cells. Data is represented as the mean values±SEM of two independent experiments.

To evaluate the effect of KLF4 activation on cell cycle distribution, DNA content was analyzed by flow cytometry in cells stained with propidium iodide (PI) following dsKLF4-496 transfection. In PC-3 cells, dsKLF4-496 caused a significant increase in G1/G0 populations with concurrent declines in S and G2/M populations as compared to control treatments (FIG. 19, panels A and C). Arrest in G2/M phase was associated with KLF4 activation in DuPro cells with proportional declines in S and G1/G0 populations (FIG. 19, panels B and D). KLF4 overexpression by dsKLF4-496 also led to a subtle increase in cells with sub-diploid (<2C) DNA content; a marker for DNA fragmentation/apoptosis (FIG. 19, panels A-D). Interestingly, we also observed cell populations in dsKLF4-496 transfected cells with DNA content exceeding levels found in mitotic cells (>4C) (FIG. 19, panels A-D). Cell populations with increased ploidy may reflect defective cytokinesis resulting from the downregulation of CENPE and/or BUB1B (FIG. 18, panels D and E). In support, multinucleated cells were routinely observed in images taken of cells transfected with dsKLF4-496. Taken together, these results indicate the antigrowth effect of KLF4 overexpression by dsKLF4-496 in prostate cancer cells is mainly mediated by modulating cell cycle genes leading to arrested cell cycle progression.

Example 13

Figure 20:
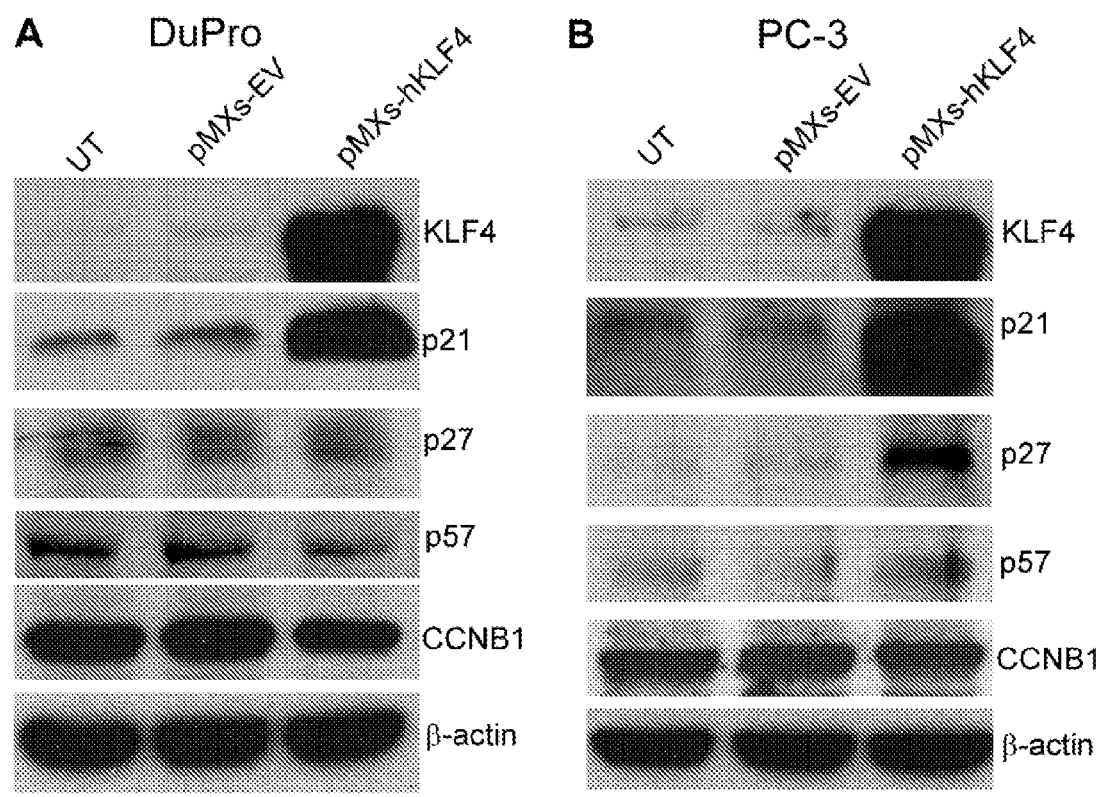
FIG. 20 shows vector-based overexpression of KLF4 and modulation of downstream cell cycle genes. Panels A and B. DuPro (A) and PC-3 (B) cells were infected with retroviral particles generated from an empty control vector (pMXs-EV) or a vector expressing human KLF4 cDNA (pMXs-hKLF4). Untreated (UT) controls were grown in absence of infection. Four days following transduction, protein was isolated for immunoblot analysis of KLF4, p21, p27, p57, CCNB1 and β-actin. β-actin served as a loading control.

Vector-Based Overexpression of KLF4 Recapitulated RNAa Results and Validated the Role of KLF4 as a Negative Regulator of Cell Proliferation To validate the results obtained through RNAa-mediated activation of KLF4, a retroviral transduction system was utilized to overexpress KLF4 cDNA (pMXs-hKLF4) in prostate cancer cell lines. Infection of KLF4 viral particles caused robust induction of KLF4 protein levels and modulation of several downstream target genes (i.e. 21, p27, p57, and CCNB1) in a pattern similar to RNA-mediated KLF4 overexpression (FIG. 20). Significantly, p21 was dramatically induced in pMXs-hKLF4 transduced DuPro (FIG. 20, panel A) and PC-3 (FIG. 20, panel B) cells. Similar to a reduction in protein expression in DuPro cells caused by RNAa (FIG. 18, panel A), p57 protein level was also downregulated in DuPro cells by ectopic expression of KLF4 (FIG. 20, panel A). On the other hand, the downregulation of CCNB1 in DuPro and PC-3 cells and the upregulation of p57 in PC-3 cells by ectopic expression of KLF4 (FIG. 20, panels A and B) were noticeably less in magnitude compared to that caused by RNAa (FIG. 18, panels A and B) despite significantly higher KLF4 levels by viral transduction (FIG. 20, panels A and B). These findings suggest that RNAa has restored a functional KLF4 protein more potent in regulating transcription of its downstream genes. Morphologically, viral transduction of KLF4 caused changes consistent with growth inhibition, as well as a noticeable presence of multinucleated cells. Functional studies in PC-3 and DuPro cells revealed that KLF4 transduction decreased cell viability and colony forming potential as compared to control treatments. Vector-based overexpression of KLF4 thus recapitulated the results obtained by RNAa-mediated KLF4 induction. This data validates RNAa as a technique to study KLF4 function and confirms its role as a putative tumor suppressor in prostate cancer cells.

References (The Following References Pertain to Examples 9-13 Above)

1. Li L C, Okino S T, Zhao H, et al. Small dsRNAs induce transcriptional activation in human cells. Proceedings of the National Academy of Sciences of the United States of America 2006 Nov. 14; 103(46):17337-42.
2. Janowski B A, Younger S T, Hardy D B, Ram R, Huffman K E, Corey D R. Activating gene expression in mammalian cells with promoter-targeted duplex RNAs. Nature chemical biology 2007 March; 3(3):166-73.
3. Place R F, Li L C, Pookot D, Noonan E J, Dahiya R. MicroRNA-373 induces expression of genes with complementary promoter sequences. Proceedings of the National Academy of Sciences of the United States of America 2008 Feb. 5; 105(5):1608-13.
4. Morris K V, Chan S W, Jacobsen S E, Looney D J. Small interfering RNA-induced transcriptional gene silencing in human cells. Science 2004 Aug. 27; 305(5688):1289-92.
5. Janowski B A, Huffman K E, Schwartz J C, et al. Inhibiting gene expression at transcription start sites in chromosomal DNA with antigene RNAs. Nat Chem Biol 2005 September; 1(4):216-22.
6. Kim D H, Villeneuve L M, Morris K V, Rossi J J. Argonaute-1 directs siRNA-mediated transcriptional gene silencing in human cells. Nature structural & molecular biology 2006 September; 13(9):793-7.
7. Napoli S, Pastori C, Magistri M, Carbone G M, Catapano C V. Promoter-specific transcriptional interference and c-myc gene silencing by siRNAs in human cells. Embo J 2009 May 21.
8. Kim D H, Saetrom P, Snove O, Jr., Rossi J J. MicroRNA-directed transcriptional gene silencing in mammalian cells. Proc Natl Acad Sci USA 2008 Oct. 21; 105(42):16230-5.
9. Evans P M, Zhang W, Chen X, Yang J, Bhakat K K, Liu C. Kruppel-like factor 4 is acetylated by p300 and regulates gene transcription via modulation of histone acetylation. J Biol Chem 2007 Nov. 23; 282(47):33994-4002.
10. Shields J M, Christy R J, Yang V W. Identification and characterization of a gene encoding a gut-enriched Kruppel-like factor expressed during growth arrest. J Biol Chem 1996 Aug. 16; 271(33):20009-17.
11. Zhao W, Hisamuddin I M, Nandan M O, Babbin B A, Lamb N E, Yang V W. Identification of Kruppel-like factor 4 as a potential tumor suppressor gene in colorectal cancer. Oncogene 2004 Jan. 15; 23(2):395-402.

12. Wei D, Gong W, Kanai M, et al. Drastic down-regulation of Kruppel-like factor 4 expression is critical in human gastric cancer development and progression. Cancer Res 2005 Apr. 1; 65(7):2746-54.
13. Ghaleb A M, McConnell B B, Nandan M O, Katz J P, Kaestner K H, Yang V W. Haploinsufficiency of Kruppel-like factor 4 promotes adenomatous polyposis coli dependent intestinal tumorigenesis. Cancer Res 2007 Aug. 1; 67(15):7147-54.
14. Wei D, Kanai M, Jia Z, Le X, Xie K. Kruppel-like factor 4 induces p27Kip1 expression in and suppresses the growth and metastasis of human pancreatic cancer cells. Cancer Res 2008 Jun. 15; 68(12):4631-9.
15. Rhodes D R, Kalyana-Sundaram S, Mahavisno V, et al. Oncomine 3.0: genes, pathways, and networks in a collection of 18,000 cancer gene expression profiles. Neoplasia 2007 February; 9(2):166-80.
16. Tomlins S A, Mehra R, Rhodes D R, et al. Integrative molecular concept modeling of prostate cancer progression. Nat Genet. 2007 January; 39(1):41-51.
17. Dhanasekaran S M, Barrette T R, Ghosh D, et al. Delineation of prognostic biomarkers in prostate cancer. Nature 2001 Aug. 23; 412(6849):822-6.
18. Vanaja D K, Cheville J C, Iturria S J, Young C Y. Transcriptional silencing of zinc finger protein 185 identified by expression profiling is associated with prostate cancer progression. Cancer Res 2003 Jul. 15; 63(14):3877-82.
19. Varambally S, Yu J, Laxman B, et al. Integrative genomic and proteomic analysis of prostate cancer reveals signatures of metastatic progression. Cancer Cell 2005 November; 8(5):393-406.
20. Dhanasekaran S M, Dash A, Yu J, et al. Molecular profiling of human prostate tissues: insights into gene expression patterns of prostate development during puberty. Faseb J 2005 February; 19(2):243-5.
21. Ramaswamy S, Tamayo P, Rifkin R, et al. Multiclass cancer diagnosis using tumor gene expression signatures. Proc Natl Acad Sci USA 2001 Dec. 18; 98(26):15149-54.
22. Ramaswamy S, Ross K N, Lander E S, Golub T R. A molecular signature of metastasis in primary solid tumors. Nat Genet. 2003 January; 33(1):49-54.
23. Yu Y P, Landsittel D, Jing L, et al. Gene expression alterations in prostate cancer predicting tumor aggression and preceding development of malignancy. J Clin Oncol 2004 Jul. 15; 22(14):2790-9.
24. True L, Coleman I, Hawley S, et al. A molecular correlate to the Gleason grading system for prostate adenocarcinoma. Proc Natl Acad Sci USA 2006 Jul. 18; 103(29): 10991-6.
25. Kharas M G, Yusuf I, Scarfone V M, et al. KLF4 suppresses transformation of pre-B cells by ABL oncogenes. Blood 2007 Jan. 15; 109(2):747-55.
26. Hu W, Hofstetter W L, Li H, et al. Putative tumor-suppressive function of Kruppel-like factor 4 in primary lung carcinoma. Clin Cancer Res 2009 Sep. 15; 15(18):5688-95.
27. Chen X, Whitney E M, Gao S Y, Yang V W. Transcriptional profiling of Kruppel-like factor 4 reveals a function in cell cycle regulation and epithelial differentiation. J Mol Biol 2003 Feb. 21; 326(3):665-77.
28. Rowland B D, Bernards R, Peeper D S. The KLF4 tumour suppressor is a transcriptional repressor of p53 that acts as a context-dependent oncogene. Nat Cell Biol 2005 November; 7(11):1074-82.
29. Chen X, Johns D C, Geiman D E, et al. Kruppel-like factor 4 (gut-enriched Kruppel-like factor) inhibits cell proliferation by blocking G1/S progression of the cell cycle. J Biol Chem 2001 Aug. 10; 276(32):30423-8.
30. Zhang W, Geiman D E, Shields J M, et al. The gut-enriched Kruppel-like factor (Kruppel-like factor 4) mediates the transactivating effect of p53 on the p21WAF1/Cip1 promoter. J Biol Chem 2000 Jun. 16; 275(24):18391-8.
31. Hagos E G, Ghaleb A M, Dalton W B, Bialkowska A B, Yang V W. Mouse embryonic fibroblasts null for the Kruppel-like factor 4 gene are genetically unstable. Oncogene 2009 Mar. 5; 28(9):1197-205.
32. Turunen M P, Lehtola T, Heinonen S E, et al. Efficient regulation of VEGF expression by promoter-targeted lentiviral shRNAs based on epigenetic mechanism: a novel example of epigenetherapy. Circ Res 2009 Sep. 11; 105(6): 604-9.
33. Wei D, Kanai M, Huang S, Xie K. Emerging role of KLF4 in human gastrointestinal cancer. Carcinogenesis 2006 January; 27(1):23-31.
34. Evans P M, Liu C. Roles of Krupel-like factor 4 in normal homeostasis, cancer and stem cells. Acta Biochim Biophys Sin(Shanghai) 2008 July; 40(7):554-64.
35. Dang D T, Chen X, Feng J, Torbenson M, Dang L H, Yang V W. Overexpression of Kruppel-like factor 4 in the human colon cancer cell line RKO leads to reduced tumorigenecity. Oncogene 2003 May 29; 22(22):3424-30.
36. Wassmann S, Wassmann K, Jung A, et al. Induction of p53 by GKLF is essential for inhibition of proliferation of vascular smooth muscle cells. J Mol Cell Cardiol 2007 September; 43(3):301-7.
37. Katz J P, Perreault N, Goldstein B G, et al. Loss of Klf4 in mice causes altered proliferation and differentiation and precancerous changes in the adult stomach. Gastroenterology 2005 April; 128(4):935-45.
38. Nakahara Y, Northcott P A, Li M, et al. Genetic and epigenetic inactivation of Kruppel-like factor 4 in medulloblastoma. Neoplasia 2010 January; 12(1):20-7.
39. Akaogi K, Nakajima Y, Ito I, et al. KLF4 suppresses estrogen-dependent breast cancer growth by inhibiting the transcriptional activity of ERalpha. Oncogene 2009 Aug. 13; 28(32):2894-902.
40. Foster K W, Liu Z, Nail C D, et al. Induction of KLF4 in basal keratinocytes blocks the proliferation-differentiation switch and initiates squamous epithelial dysplasia. Oncogene 2005 Feb. 24; 24(9):1491-500.
41. Huang C C, Liu Z, Li X, et al. KLF4 and PCNA identify stages of tumor initiation in a conditional model of cutaneous squamous epithelial neoplasia. Cancer Biol Ther 2005 December; 4(12):1401-8.
42. Yang Y, Goldstein B G, Chao H H, Katz J P. KLF4 and KLF5 regulate proliferation, apoptosis and invasion in esophageal cancer cells. Cancer Biol Ther 2005 November; 4(11):1216-21.
43. Tian Y, Luo A, Cai Y, et al. MICRORNA-10B promotes human esophageal cancer cell migration and invasion through KLF4. J Biol Chem 2010 January 14.
44. Yoon H S, Chen X, Yang V W. Kruppel-like factor 4 mediates p53-dependent G1/S cell cycle arrest in response to DNA damage. J Biol Chem 2003 Jan. 24; 278(4):2101-5.
45. Yoon H S, Yang V W. Requirement of Kruppel-like factor 4 in preventing entry into mitosis following DNA damage. J Biol Chem 2004 Feb. 6; 279(6):5035-41.
46. Rowland B D, Peeper D S. KLF4, p21 and context-dependent opposing forces in cancer. Nat Rev Cancer 2006 January; 6(1):11-23.

47. Bunz F, Dutriaux A, Lengauer C, et al. Requirement for p53 and p21 to sustain G2 arrest after DNA damage. Science 1998 Nov. 20; 282(5393):1497-501.
48. Matsuoka S, Edwards M C, Bai C, et al. p57KIP2, a structurally distinct member of the p21CIP1 Cdk inhibitor family, is a candidate tumor suppressor gene. Genes Dev 1995 Mar. 15; 9(6):650-62.
49. Ghaleb A M, Katz J P, Kaestner K H, Du J X, Yang V W. Kruppel-like factor 4 exhibits antiapoptotic activity following gamma-radiation-induced DNA damage. Oncogene 2007 Apr. 5; 26(16):2365-73.
50. Brinster R L, Allen J M, Behringer R R, Gelinas R E, Palmiter R D. Introns increase transcriptional efficiency in transgenic mice. Proc Natl Acad Sci USA 1988 February; 85(3):836-40.
51. Clark A J, Archibald A L, McClenaghan M, Simons J P, Wallace R, Whitelaw C B. Enhancing the efficiency of transgene expression. Philos Trans R Soc Lond B Biol Sci 1993 Feb. 27; 339(1288):225-32.
52. Stemmler M P, Hecht A, Kemler R. E-cadherin intron 2 contains cis-regulatory elements essential for gene expression. Development 2005 March; 132(5):965-76.
53. Breitbart R E, Nguyen H T, Medford R M, Destree A T, Mandavi V, Nadal-Ginard B. Intricate combinatorial patterns of exon splicing generate multiple regulated troponin T isoforms from a single gene. Cell 1985 May; 41(1):67-82.
54. Leff S E, Rosenfeld M G, Evans R M. Complex transcriptional units: diversity in gene expression by alternative RNA processing. Annu Rev Biochem 1986; 55:1091-117.
55. Thierry-Mieg D, Thierry-Mieg J. AceView: a comprehensive cDNA-supported gene and transcripts annotation. Genome Biol 2006; 7 Suppl 1:S12 1-4.
56. Li L C, Dahiya R. MethPrimer: designing primers for methylation PCRs. Bioinformatics 2002 November; 18(11):1427-31.
57. Takahashi K, Tanabe K, Ohnuki M, et al. Induction of pluripotent stem cells from adult human fibroblasts by defined factors. Cell 2007 Nov. 30; 131(5):861-72.

That which is claimed is:

1. An isolated composition comprising, a small activating RNA (saRNA) molecule comprising at least a first ribonucleic acid strand comprising a sequence selected from SEQ ID NO: 1, SEQ ID NO: 2, SEQ ID NO: 3, and SEQ ID NO: 4, wherein the sequence is complementary to a promoter region sequence of a NKX3-1 gene and is sufficient to activate transcription of the NKX3-1 gene.

2. The composition of claim 1, wherein the saRNA molecule comprises a second ribonucleic acid strand and wherein when the first ribonucleic acid strand comprises a sequence from SEQ ID NO: 1, the second ribonucleic acid strand comprises a sequence from SEQ ID NO: 2 and when the first ribonucleic acid strand comprises a sequence from SEQ ID NO: 3, the second ribonucleic acid strand comprises a sequence from SEQ ID NO: 4.

3. The composition of claim 1, wherein the saRNA molecule comprises a thio modified internucleotide linkage.

4. The composition of claim 1, wherein the composition comprises a second saRNA molecule comprising at least one ribonucleic acid strand, wherein when the first ribonucleic acid strand comprises a sequence from SEQ ID NO: 1, the one ribonucleic acid strand of the second saRNA comprises a sequence from SEQ ID NO: 3 or SEQ ID NO: 4.

5. The composition of claim 4, wherein when the one ribonucleic acid strand of the second saRNA comprises a sequence from SEQ ID NO: 3, another ribonucleic acid strand of the second saRNA strand comprises a sequence from SEQ ID NO: 4.

6. The composition of claim 1, wherein the composition further comprises at least one of a pharmaceutically acceptable carrier, a pharmaceutically acceptable diluent, a pharmaceutically acceptable excipient and a pharmaceutically acceptable adjuvant.

7. A kit comprising, a small activating RNA (saRNA) molecule comprising at least a first ribonucleic acid strand comprising a sequence selected from SEQ ID NO: 1, SEQ ID NO: 2, SEQ ID NO: 3, and SEQ ID NO: 4, wherein the sequence is complementarity to a promoter region sequence of a NKX3-1 gene and is sufficient to activate transcription of the NKX3-1 gene.

8. The kit of claim 7, wherein the saRNA molecule comprises a second ribonucleic acid strand and wherein when the first ribonucleic acid strand comprises a sequence from SEQ ID NO: 1, the second ribonucleic acid strand comprises a sequence from SEQ ID NO: 2 and when the first ribonucleic acid strand comprises a sequence from SEQ ID NO: 3, the second ribonucleic acid strand comprises a sequence from SEQ ID NO: 4.

9. The kit of claim 7, wherein the kit comprises a second saRNA molecule comprising at least one ribonucleic acid strand, wherein when the first ribonucleic acid strand comprises a sequence from SEQ ID NO: 1, the one ribonucleic acid strand of the second saRNA comprises a sequence from SEQ ID NO: 3 or SEQ ID NO: 4.

10. The kit of claim 9, wherein when the one ribonucleic acid strand of the second saRNA comprises a sequence from SEQ ID NO: 3, another ribonucleic acid strand of the second saRNA strand comprises a sequence from SEQ ID NO: 4.

11. The kit of claim 7, wherein the saRNA molecule comprises a thio modified internucleotide linkage.

12. The kit of claim 7, wherein the kit further comprises at least one of a pharmaceutically acceptable carrier, a pharmaceutically acceptable diluent, a pharmaceutically acceptable excipient and a pharmaceutically acceptable adjuvant.

13. A method to increase expression of a gene comprising:
introducing a small activating RNA (saRNA) molecule into a mammalian cell in an amount sufficient to increase expression of a NKX3-1 gene, wherein the saRNA molecule comprises at least a first ribonucleic acid strand comprising,
a sequence selected from SEQ ID NO: 1, SEQ ID NO: 2, SEQ ID NO: 3, and SEQ ID NO: 4,
wherein the sequence is complementary to a promoter region sequence of the NKX3-1 gene, and
wherein the introducing results in an increase in expression of the NKX3-1 gene.

14. The method of claim 13, wherein the saRNA molecule comprises a second ribonucleic acid and wherein when the first ribonucleic acid strand comprises a sequence from SEQ ID NO: 1, the second ribonucleic acid strand comprises a sequence from SEQ ID NO: 2 and when the first ribonucleic acid strand comprises a sequence from SEQ ID NO: 3, the second ribonucleic acid strand comprises a sequence from SEQ ID NO: 4.

15. The method of claim 13, wherein the introducing comprises introducing a second saRNA molecule, the second saRNA molecule comprising at least one ribonucleic acid strand, wherein when the first ribonucleic acid strand comprises a sequence from SEQ ID NO: 1, the one ribonucleic acid strand of the second saRNA comprises a sequence from SEQ ID NO: 3 or SEQ ID NO: 4.

16. The method of claim 15, wherein when the one ribonucleic acid strand of the second saRNA comprises a sequence from SEQ ID NO: 3, another ribonucleic acid strand of the second saRNA strand comprises a sequence from SEQ ID NO: 4.

17. The method of claim 13, wherein the saRNA molecule is introduced into the mammalian cell by introducing of a nucleic acid vector encoding the saRNA molecule.

18. The method of claim 13, wherein the saRNA molecule comprises a thio modified internucleotide linkage.

19. A method of reducing proliferation of a cell in a subject having a cellular proliferative disease comprising,
administering to the subject an effective amount of a small activating RNA (saRNA) molecule, wherein the saRNA molecule comprises at least a first ribonucleic acid strand comprising
a sequence selected from SEQ ID NO: 1, SEQ ID NO: 2, SEQ ID NO: 3, and SEQ ID NO: 4,
wherein the sequence is complementarity to a promoter region sequence of a NKX3-1 gene, and
wherein the administering provides for an increase in expression of NKX3-1 polypeptide and a decrease in cellular proliferation.

20. The method of claim 19, wherein the saRNA molecule comprises a second ribonucleic acid strand and wherein when the first ribonucleic acid strand comprises a sequence from SEQ ID NO: 1, the second ribonucleic acid strand comprises a sequence from SEQ ID NO: 2 and when the first ribonucleic acid strand comprises a sequence from SEQ ID NO: 3, the second ribonucleic acid strand comprises a sequence from SEQ ID NO: 4.

21. The method of claim 19, wherein the administering comprises administering a second saRNA molecule, the second saRNA molecule comprising at least one ribonucleic acid strand, wherein when the first ribonucleic acid strand comprises a sequence from SEQ ID NO: 1, the one ribonucleic acid strand of the second saRNA comprises a sequence from SEQ ID NO: 3 or SEQ ID NO: 4.

22. The method of claim 21, wherein when the one ribonucleic acid strand of the second saRNA comprises a sequence from SEQ ID NO: 3, another ribonucleic acid strand of the second saRNA strand comprises a sequence from SEQ ID NO: 4.

23. The method of claim 19, wherein the saRNA molecule is introduced into the mammalian cell by introducing of a nucleic acid vector encoding the saRNA molecule.

24. The method of claim 19, wherein the saRNA molecule comprises a thio modified internucleotide linkage.

25. The method of claim 19, wherein the cellular proliferative disease is prostate cancer.

* * * * *